(12) United States Patent
Nashman et al.

(10) Patent No.: US 12,306,276 B2
(45) Date of Patent: May 20, 2025

(54) SYSTEM AND METHOD FOR NUCLEAR MAGNETIC RESONANCE CALIBRATION

(71) Applicant: Synex Medical Inc., Toronto (CA)

(72) Inventors: Benjamin Saul Nashman, Toronto (CA); Sean Kentaro Sullivan Takahashi, Toronto (CA)

(73) Assignee: Synex Medical Inc., Toronto (CA)

( * ) Notice: Subject to any disclaimer, the term of this patent is extended or adjusted under 35 U.S.C. 154(b) by 0 days.

(21) Appl. No.: 18/503,909

(22) Filed: Nov. 7, 2023

(65) Prior Publication Data

US 2024/0151794 A1    May 9, 2024

Related U.S. Application Data

(60) Provisional application No. 63/423,733, filed on Nov. 8, 2022.

(51) Int. Cl.
| | | |
|---|---|---|
| *G01R 33/465* | (2006.01) | |
| *A61B 5/055* | (2006.01) | |
| *A61B 5/145* | (2006.01) | |
| *G01R 33/00* | (2006.01) | |
| *G01R 33/44* | (2006.01) | |
| *G01R 33/46* | (2006.01) | |
| *G01R 33/54* | (2006.01) | |
| *G01R 33/58* | (2006.01) | |

(52) U.S. Cl.
CPC ............ *G01R 33/465* (2013.01); *A61B 5/055* (2013.01); *A61B 5/14532* (2013.01); *G01R 33/0035* (2013.01); *G01R 33/443* (2013.01); *G01R 33/4625* (2013.01); *G01R 33/543* (2013.01); *G01R 33/583* (2013.01)

(58) Field of Classification Search
CPC .. A61B 5/055; A61B 5/14532; G01R 33/443; G01R 33/583; G01R 33/465
See application file for complete search history.

(56) References Cited

U.S. PATENT DOCUMENTS

| | | |
|---|---|---|
| 7,405,567 B2 | 7/2008 | McDowell |
| 9,285,441 B1 | 3/2016 | McDowell |

(Continued)

FOREIGN PATENT DOCUMENTS

WO     2012122462 A2     9/2012

OTHER PUBLICATIONS

Lee et al. "Prospective frequency correction using outer volume suppression-localized navigator for MR spectroscopy and spectroscopic imaging" Magnetic Resonance in Medicine 2366-2373 (2018). (Year: 2018).*

(Continued)

*Primary Examiner* — Angela M Hoffa

(74) *Attorney, Agent, or Firm* — Jeffrey Schox; Annie Imbrie-Moore

(57) ABSTRACT

In variants, the system (e.g., a nuclear magnetic resonance system) can include: a magnet array, a housing, a transmitter, a receiver, and a processing system. In variants, the method can include: sampling a calibration measurement, determining a reference frequency based on the calibration measurement, and sampling an experiment measurement. The method can optionally include: processing the experiment measurement, determining an analyte level, and/or any other suitable steps.

13 Claims, 18 Drawing Sheets

(56) References Cited

U.S. PATENT DOCUMENTS

| | | | |
|---|---|---|---|
| 10,739,428 | B2 | 8/2020 | McDowell |
| 10,845,441 | B1 | 11/2020 | McDowell |
| 11,204,405 | B1 | 12/2021 | McDowell |
| 11,317,822 | B2 * | 5/2022 | Nashman ............ A61B 5/14532 |
| 11,793,429 | B2 * | 10/2023 | Nashman ............... A61B 5/742 |
| 11,931,137 | B2 * | 3/2024 | Nashman ............. A61B 5/7203 |
| 2013/0320979 | A1 * | 12/2013 | Yang .................... G01R 33/485 |
| | | | 324/318 |
| 2015/0253401 | A1 * | 9/2015 | Rapoport ............... G01R 33/48 |
| | | | 324/318 |
| 2016/0011290 | A1 * | 1/2016 | Iannello ................. A61B 5/055 |
| | | | 600/422 |
| 2016/0327626 | A1 * | 11/2016 | Ha ........................ G01R 33/443 |
| 2020/0367795 | A1 * | 11/2020 | Qian ....................... A61B 5/681 |
| 2021/0121108 | A1 * | 4/2021 | Nashman ........... G01R 33/3873 |
| 2021/0196143 | A1 | 7/2021 | O'Brien |
| 2025/0049343 | A1 * | 2/2025 | Nashman ............. A61B 5/6826 |
| 2025/0049351 | A1 * | 2/2025 | Nashman ............. G01R 33/341 |

OTHER PUBLICATIONS

Benner et al. "Real-Time RF Pulse Adjustment for B0 Drift Correction" Magnetic Resonance in Medicine 56:204-209 (2006). (Year: 2006).*

Ebel et al. "Detection and Correction of Frequency Instabilities for Volumetric 1H Echo-Planar Spectroscopic Imaging" Magnetic Resonance in Medicine 53:465-469 (2005). (Year: 2005).*

Pouliot et al. "Investigations of optical pumping for magnetometry using an auto-locking laser system" Conference Paper, 9 pages (May 2018). (Year: 2018).*

Keating et al. "Real-Time Dynamic Frequency and Shim Correction for Single-Voxel Magnetic Resonance Spectroscopy" Magnetic Resonance in Medicine 68: 1339-1345 (2012). (Year: 2012).*

Lange et al. "Correction of Frequency Drifts Induced by Gradient Heating in 1H Spectra Using Interleaved Reference Spectroscopy". Journal of Magnetic Resonance Imaging 33:748-754 (2011). (Year: 2011).*

Rimal, Vaclav, et al., "Correction of field instabilities in biomolecular solid-state NMR by simul-taneous acquisition of a frequency reference", Supplement of Magn. Reson., 3, 15-26, 2022.

Rimal, Viclav, et al., "Correction of field instabilities in biomolecular solid-state NMR by simultaneous acquisition of a frequency reference", Magn. Reson., 3, 15-26, 2022.

* cited by examiner

SYSTEM AND METHOD FOR NUCLEAR MAGNETIC RESONANCE CALIBRATION

CROSS-REFERENCE TO RELATED APPLICATIONS

This application claims the benefit of U.S. Provisional Application No. 63/423,733 filed 8 Nov. 2022, which is incorporated in its entirety by this reference.

TECHNICAL FIELD

This invention relates generally to the nuclear magnetic resonance field, and more specifically to a new and useful system and method in the nuclear magnetic resonance field.

DETAILED DESCRIPTION

The following description of the embodiments of the invention is not intended to limit the invention to these embodiments, but rather to enable any person skilled in the art to make and use this invention.

1. OVERVIEW

Figure 1:
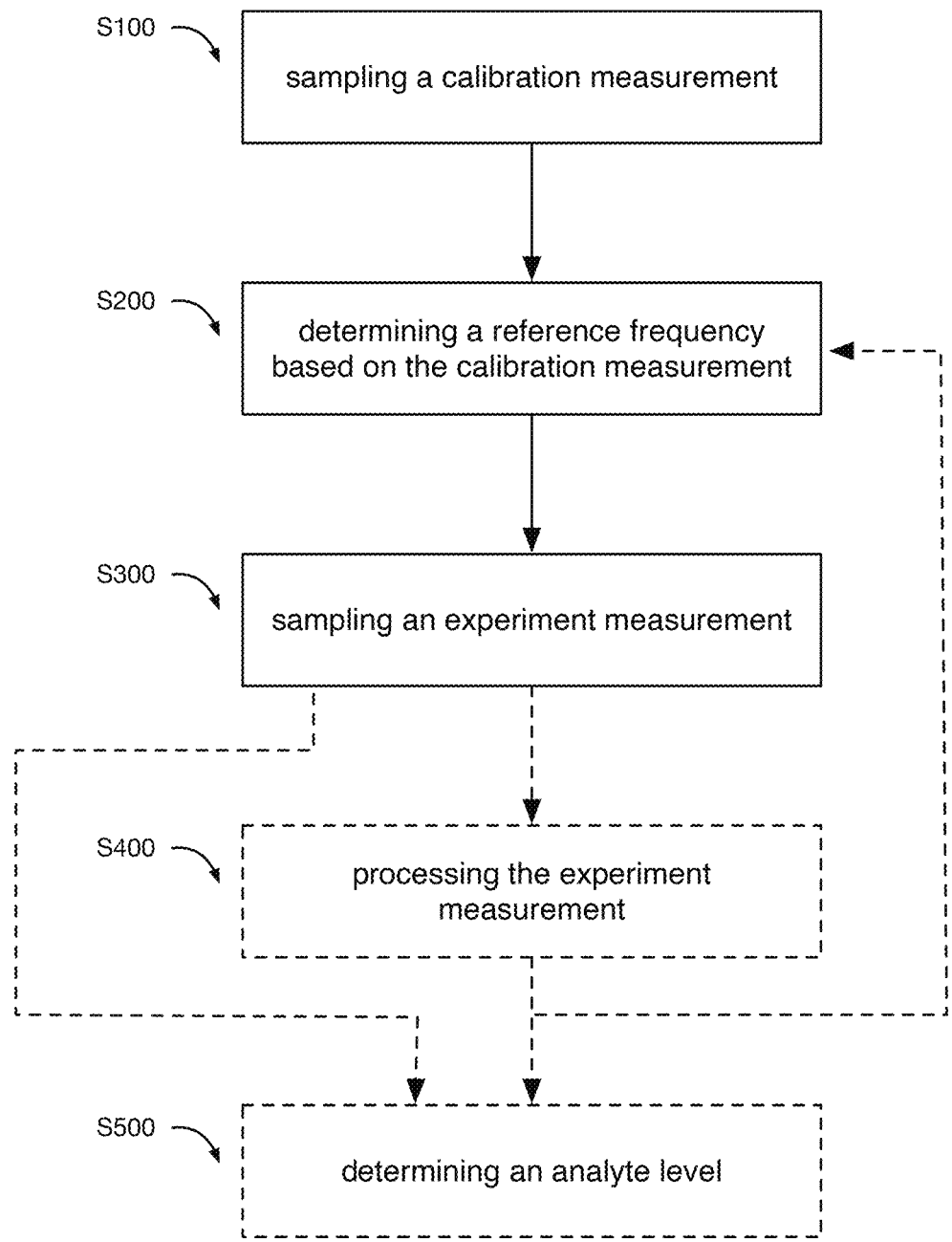
FIG. 1 is a schematic representation of a variant of the method.

As shown in FIG. 1, the method can include: sampling a calibration measurement S100, determining a reference frequency based on the calibration measurement S200, and sampling an experiment measurement S300. However, the method can additionally or alternatively include any other suitable steps.

Figure 2:
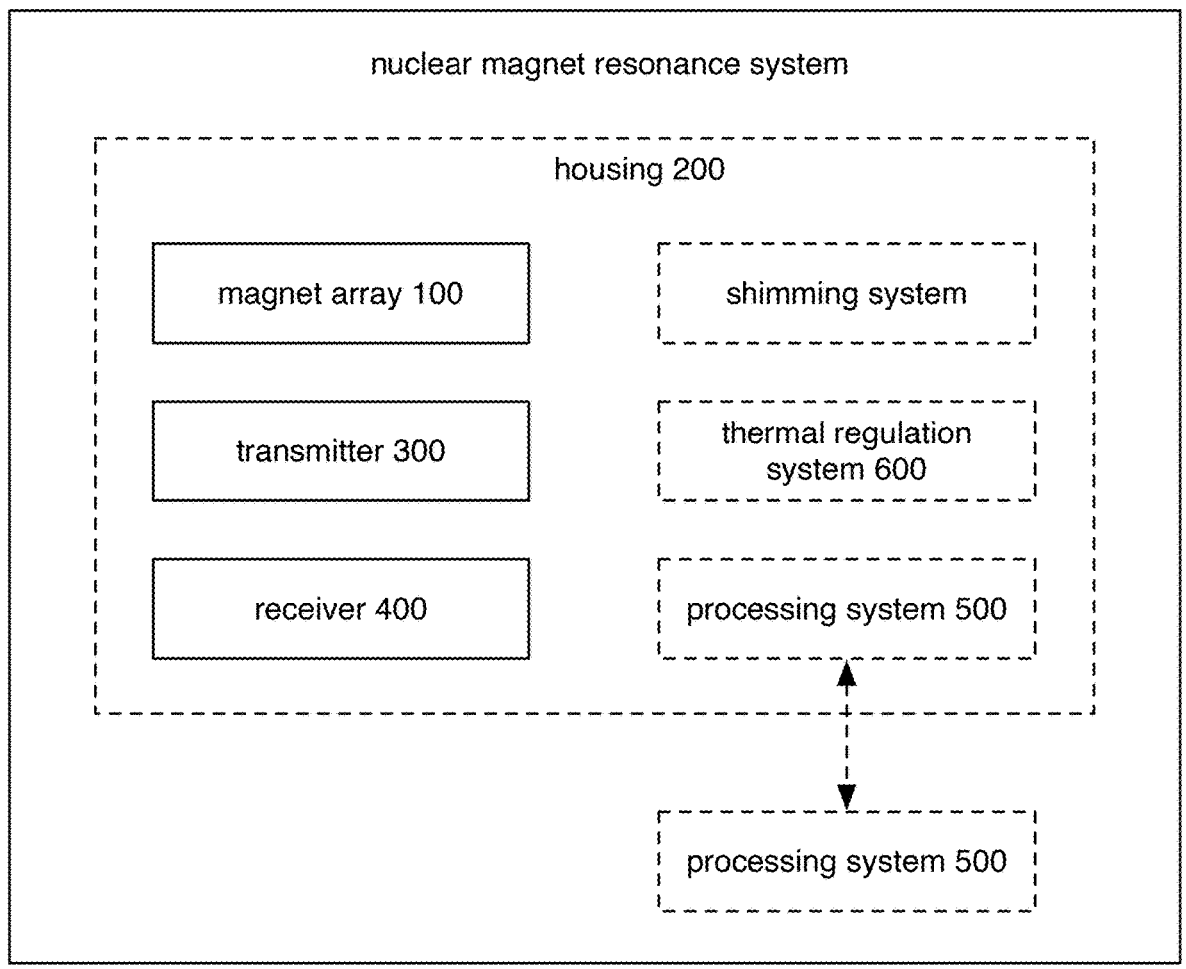
FIG. 2 is a schematic representation of a variant of the system.

As shown in FIG. 2, the system (e.g., a nuclear magnetic resonance system) can include: a magnet array 100, a housing 200, a transmitter 300, a receiver 400, and a processing system 500. However, the system and additionally or alternatively include any other suitable components.

In variants, the system and/or method can function to calibrate a nuclear magnetic resonance system for temperature (e.g., temperature drift) and/or other factors. In specific example, the system and method can function to adjust transmission parameters to account for temperature, process measurements to account for temperature, and/or otherwise calibrate the nuclear magnetic resonance system. The system and/or method can additionally or alternatively function to characterize blood analyte levels within a sample (e.g., a finger).

2. EXAMPLES

In an example, the method can include: using a nuclear magnetic resonance (NMR) system, transmitting a first transmission (e.g., into a measurement volume); sampling a first measurement from a sample (e.g., a finger) in response to the first transmission; determining a reference frequency based on the first measurement; determining transmission parameters (e.g., a characteristic frequency) for a second transmission based on the reference frequency; transmitting the second transmission (e.g., into the measurement volume); and sampling a second measurement from the sample in response to the second transmission. The reference frequency can optionally be determined by fitting a function to a segment of the first measurement, and determining the reference frequency based on the fitted function (e.g., the frequency at the maximum of the function). The method can optionally be performed for one or more subsequent iterations, wherein each subsequent transmission can be determined based on one or more reference frequencies for previously sampled measurements. The method can optionally include processing a measurement using reference frequencies for: prior measurements, the current measurement, and/or subsequent measurements. For example, a (linear or nonlinear) frequency drift can be determined based on the reference frequencies, wherein a corrective filter can be determined based on the frequency drift and applied to the measurement for correction (e.g., to correct for temperature drift during second measurement sampling). A blood analyte level for the sample can optionally be determined based on all or a portion of the sampled measurements.

3. TECHNICAL ADVANTAGES

Variants of the technology can confer one or more advantages over conventional technologies.

First, the Larmor frequency (e.g., resonant frequency) for a permanent magnet nuclear magnetic resonance (NMR) system and sample is highly sensitive to temperature. Conventional permanent magnet NMR systems often reduce frequency drift due to temperature change by using a temperature-controlled measurement chamber (e.g., set to a constant high temperature). However, with a small-scale NMR system (e.g., less than 1,000 cm$^3$ volume, less than 5 kg weight, etc.), the Larmor frequency is more sensitive to temperature and temperature-controlled chambers are not as effective at mitigating frequency drift. Additionally, the temperature-control systems increase the size and weight of the overall NMR system. Variants of the technology can calibrate an NMR system using software instead of or in addition to using temperature-control systems. In examples, calibrating the NMR system can include correcting frequency drift prior to applying an experiment transmission (e.g., by adjusting transmitter parameters) and/or correcting for frequency drift after sampling an experiment measurement (e.g., post-processing the experiment measurement).

Second, variants of the technology can increase calibration accuracy by using a small tip angle during a calibration phase such that the sample more quickly recovers to thermal equilibrium for an experiment phase. This can reduce the delay between sampling a calibration measurement used to determine a reference frequency and applying an experiment transmission based on the reference frequency, thus resulting in an experiment transmission with a more accurate characteristic frequency (e.g., closer to the Larmor frequency). This reduced delay and/or short duration between the calibration signal and the experiment signal can also reduce the probability that the temperature (and associated Larmor frequency) has shifted between the calibration signal and the experiment signal.

However, further advantages can be provided by the system and method disclosed herein.

4. SYSTEM

As shown in FIG. 2, the system can include: a magnet array 100, a housing 200, a transmitter 300, a receiver 400, and a processing system 500. The system can optionally include: a thermal regulation system 600, a shimming system (e.g., active shims, passive shims, coarse shims, localized shims, etc.), one or more gradient coils, a user device, a user interface, and/or any other suitable components. In a specific example, the shimming system can include permanent magnets, magnetized materials, ferrous components, one or more coils, and/or any other shim component.

The magnet array 100 functions to generate a magnetic field for NMR measurements of a sample. For example, the magnet array can be configured to generate a magnetic field over a target region of the sample. The sample preferably includes a body region of a user, but can alternatively include any other in vivo sample (e.g., a body region of an animal), an in vitro sample, an inanimate sample (e.g., liquid reference sample, a phantom, etc.), and/or any other sample. The body region can include a digit (e.g., finger, toe, etc.), an extremity (e.g., arm, leg, etc.), any other appendage, and/or other body region. The sample can optionally be associated with a set of sample parameters. Examples of sample parameters include: dimensions, orientation, composition, material properties, temperature, and/or any other parameters.

The magnet array 100 preferably includes a set of permanent magnets, but can additionally or alternatively include magnetized materials, ferrous components, one or more coils, and/or any other magnetic component. The magnet array 100 can be a Halbach array (e.g., of type k=2 or any other type), a dipole, and/or any other arrangement of one or more magnets. The number of magnets in the magnet array 100 can be between 1-50 or any range or value therebetween (e.g., 2, 3, 4, 5, 6, 7, 8, 9, 10, 11, 12, 13, 14, 15, 16, greater than 2, greater than 4, etc.), but can alternatively be greater than 50. The volume of each magnet can be between 1 cm$^2$-1000 cm$^2$ or any range or value therebetween (e.g., 1 cm$^2$-100 cm$^2$, less than 100 cm$^2$, less than 50 cm$^2$, less than 20 cm$^2$, etc.), but can alternatively be less than 1 cm$^2$ or greater than 1000 cm$^2$. The magnet array 100 is preferably mounted to the housing 200, but can alternatively be mounted to any other system component. The magnet array 100 preferably applies a magnetic field (e.g., a substantially homogeneous magnetic field) over a region of interest (ROI). In a specific example, the ROI can be or include a diameter-spherical volume (DSV). The ROI preferably overlaps with a target region of the sample (e.g., the pulp of a finger), but can alternatively be otherwise configured relative to the sample. The ROI volume can be between 0.5 mm$^3$-100 cm$^3$ or any range or value therebetween (e.g., 2 mm$^3$-5 cm$^3$, 50 mm$^3$-2 cm$^3$, etc.), but can alternatively be less than 1 mm or greater than 50 mm. The field strength of the magnetic field within the ROI can be between 0.05 Tesla-2 Tesla or any range or value therebetween (e.g., 0.1 Tesla-1 Tesla, 0.25 Tesla-0.75 Tesla, 0.5 Tesla, less than 1 Tesla, less than 0.75 Tesla, less than 0.5 Tesla, etc.), but can alternatively be less than 0.05 Tesla or greater than 2 Tesla.

In a first variant, the magnet array 100 can include one or more rings, wherein each ring includes a set of magnets arranged arcuately. The set of magnets in each ring preferably cooperatively form a circle or fully surround an inner bore (e.g., an inner bore configured to received the sample, wherein the inner bore can be defined by the housing 200 and/or any other system component), but can alternatively cooperatively form part of a circle or surround a segment of the inner bore boundary. The magnet array 100 can include one or more rings and/or one ring split into two or more axial segments. The rings are preferably arranged longitudinally along the same axis (e.g., stacked), but can alternatively be otherwise arranged. In a second variant, the magnet array 100 can include a dipole, wherein each magnet in the dipole is mounted on either side of the inner bore (e.g., above and below; on the left and right sides; etc.).

However, the magnet array 100 can be otherwise configured.

The housing 200 functions to define (e.g., constrain) the position of magnets in the magnet array 100 and/or to connect and/or mount components of the system. The housing 200 encapsulates (or otherwise retains): one or more magnets in the magnet array 100, the transmitter 300, the receiver 400, all or part of the processing system 500, and/or any other system component. The housing 200 preferably defines an inner bore configured to receive the sample, wherein the ROI is within the inner bore and overlapping with the sample, but can alternatively not define the inner bore. In a specific example, the overall shape of the housing 200 can include an annular cylinder with an outer diameter and an inner bore (e.g., the inner diameter of the housing 200). However, the housing 200 can have any other shape. The housing 200 is preferably defined such that the overall NMR system is portable (e.g., a desktop device), but can alternatively be otherwise configured. The volume of the housing 200 can be between 20 cm$^3$-1 m$^3$ or any range or value therebetween (e.g., 50 cm$^3$-100,000 cm$^3$, 100 cm$^3$-10,000 cm$^3$, 500 cm$^3$-1000 cm$^3$, etc.), but can alternatively be less than 20 cm$^3$ or greater than 1 m$^3$. The housing footprint can be between 5 cm$^2$-10,000 cm$^2$ or any range or value therebetween (e.g., 10 cm$^2$-1000 cm$^2$, 50 cm$^2$-100 cm$^2$, etc.), but can alternatively be less than 5 cm$^2$ or greater than 10,000 cm². The housing 200 can optionally be potted and/or include a shield. However, the housing 200 can be otherwise configured.

The transmitter 300 functions to apply transmissions, including calibration transmissions, experiment transmissions, and/or any other transmissions. For example, the transmitter 300 can function to apply a radiofrequency (RF) sequence within the ROI, inducing magnetization in the sample. The transmitter 300 is preferably an RF transmitter, but can additionally or alternatively transmit signals of any other wavelength. Examples of transmitters and/or transmitter components include excitation coils (e.g., a solenoid), transmit probe, transmit antenna, and/or any other transmitter. One or more transmitters 300 can be arranged: along a longitudinal section of the inner bore (e.g., defined by the housing 200); arranged at or near the end (e.g., tip) of the inner bore; extend along an arcuate section of the inner bore; and/or be otherwise located. For example, the transmitter 300 can be a solenoid surrounding the inner bore (e.g., the axis of the solenoid aligns with the sample in the inner bore).

Transmitter parameters (e.g., electronics parameters for the transmitter 300) can be set to apply a transmission associated with a set of transmission parameters. The transmission is preferably a radio frequency (RF) signal (e.g., RF pulse), but can alternatively be a continuous wave and/or any other signal type. Examples of transmission parameters include: signal type, shape (e.g., square wave, trapezoidal, gaussian, etc.), frequency parameters, duration (e.g., width), amplitude, tip angle, timing parameters (e.g., pulse times, delay times, repetition times, etc.) and/or any other parameters. Transmission parameters can be static, adjustable (e.g., adjustable based on a known, predicted, or estimated reference frequency), and/or otherwise configured. The frequency parameters can include: a characteristic frequency (e.g., carrier frequency, etc.), modulation frequency, a frequency range (e.g., frequency band about the characteristic frequency), a frequency bandwidth (e.g., a width of the frequency range), a frequency pattern, and/or any other parameters. For example, a transmission can include a pulse sequence (e.g., a sequence of one or more pulses, gradients, and/or one or more delays between pulses). Types of pulses can include: adiabatic pulses, nonadiabatic pulses, Shinnar-Le Roux (SLR)-generated pulses, crusher gradient, composite pulses, hard pulses (e.g., square pulses), shaped pulses (e.g., Gaussian, sinc, truncated-sinc, etc.), excitation pulses, refocusing pulses, gradient pulses, a combination thereof, and/or any other pulse type. Examples of pulse sequences and/or pulse sequence techniques can include: gradient echo, spin echo, gradient echo train, gradient crushers (e.g., around refocusing pulses), phase cycling, CPMG, T1-filtering, T2-filtering, perfect echo, XY16, slice-selective sequencing, averaging techniques, a combination thereof, and/or any other pulse sequence and/or sequence technique.

However, the transmitter 300 can be otherwise configured.

The receiver 400 functions to sample measurements, including calibration measurements, experiment measurements, and/or any other measurements. For example, the receiver 400 can function to receive signals from excited spins in the sample. The receiver 400 is preferably an RF receiver, but can additionally or alternatively receive signals of any other wavelength. Examples of receivers and/or receiver components include receive coils, receive probe, receive antenna, and/or any other receiver. In examples, the receiver 400 can be a surface coil, a butterfly coil, a solenoid, any other coil type, and/or any receiver. The receiver 400 can optionally be positioned at or near the surface of the inner bore. One or more receivers 400 can be arranged: at a defined location along the inner bore, along a longitudinal section of the housing inner diameter and/or inner bore; arranged at or near the end (e.g., tip) of the inner bore; extend along an arcuate section of the bore; and/or be otherwise located. The receiver 400 is preferably separate and distinct from the transmitter 300, but alternatively can be the transmitter 300 (e.g., wherein the same set of coils function as a transceiver to apply an RF pulse, then measure the resultant induced voltages in the sample).

Receiver parameters (e.g., electronics parameters for the receiver 400) can be determined such that the receiver 400 can sample a measurement. The measurement can be a free induction decay (FID) and/or any other signal response in the sample in response to a transmission. Receiver parameters can include acquisition time, receiver gain, dwell time (i.e., sampling rate), and/or any other parameters defining measurement sampling. In examples, receiver parameters can be determined based on: known, estimated, and/or predicted signal parameters for a measurement (e.g., a known, estimated, and/or predicted reference frequency, echo time, relaxation times, etc.); transmission parameters; sample parameters; a signal decay rate, predetermined, random, a combination thereof, and/or otherwise determined. In an example, dwell time can be between 0.01 μs-0.01 s or any range or value therebetween (e.g., 0.1 μs-10 μs, 1 μs, etc.), but can alternatively be less than 0.01 μs or greater than 0.01 s.

However, the receiver 400 can be otherwise configured.

The system can optionally include a thermal regulation system 600, which can function to maintain all or a portion of the system at a constant temperature. This can increase measurement accuracy (e.g., by reducing field fluctuations), increase the volume of blood in the sample, improve calibration, reduce field drift (e.g., between S100 and S300, during an experiment, etc.), and/or otherwise improve system function.

In a first variant, the thermal regulation system 600 includes a heater. The heater can be located on the outside of the housing 200 (e.g., wrapping around the housing 200), integrated into the housing 200, and/or otherwise arranged relative to any system component. The heater preferably maintains all or a portion of the system at or near a target temperature, wherein the target temperature can be between 20° C.-45° C. or any range or value therebetween (e.g., 25° C.-40° C., 30° C.-37° C., 25° C., 30° C., 35° C., 37° C., 40° C., 45° C., body temperature, etc.), but can alternatively be less than 20° C. or greater than 45° C. The target temperature is preferably above room temperature, but can alternatively be at or below room temperature (e.g., wherein the thermal regulation system 600 can act as a cooling system). In a first example, the heater is a flexible printed circuit (FPC) board, wherein current passing through the board increases the temperature. Optionally, the FPC board can utilize twisted pair wiring to decrease radiation from the heater. In a second example, the heater includes one or more rigid printed circuit boards (PCB). In an illustrative example, the magnet array 100 is a dodecagonal prism (or any prism), wherein each side can be matched to a rigid PCB heater. In a second variant, the thermal regulation system 600 includes insulation for the system and/or system components. The insulation material can include: foam, potting material, plastics (e.g., PVC), and/or any other thermally insulating material. The insulation is preferably non-magnetic, but can alternatively be magnetic. In a third variant, the thermal regulation system 600 includes a combination of the previous variants, including both heating elements and insulation elements.

However, the thermal regulation system 600 can be otherwise configured.

Figure 8:
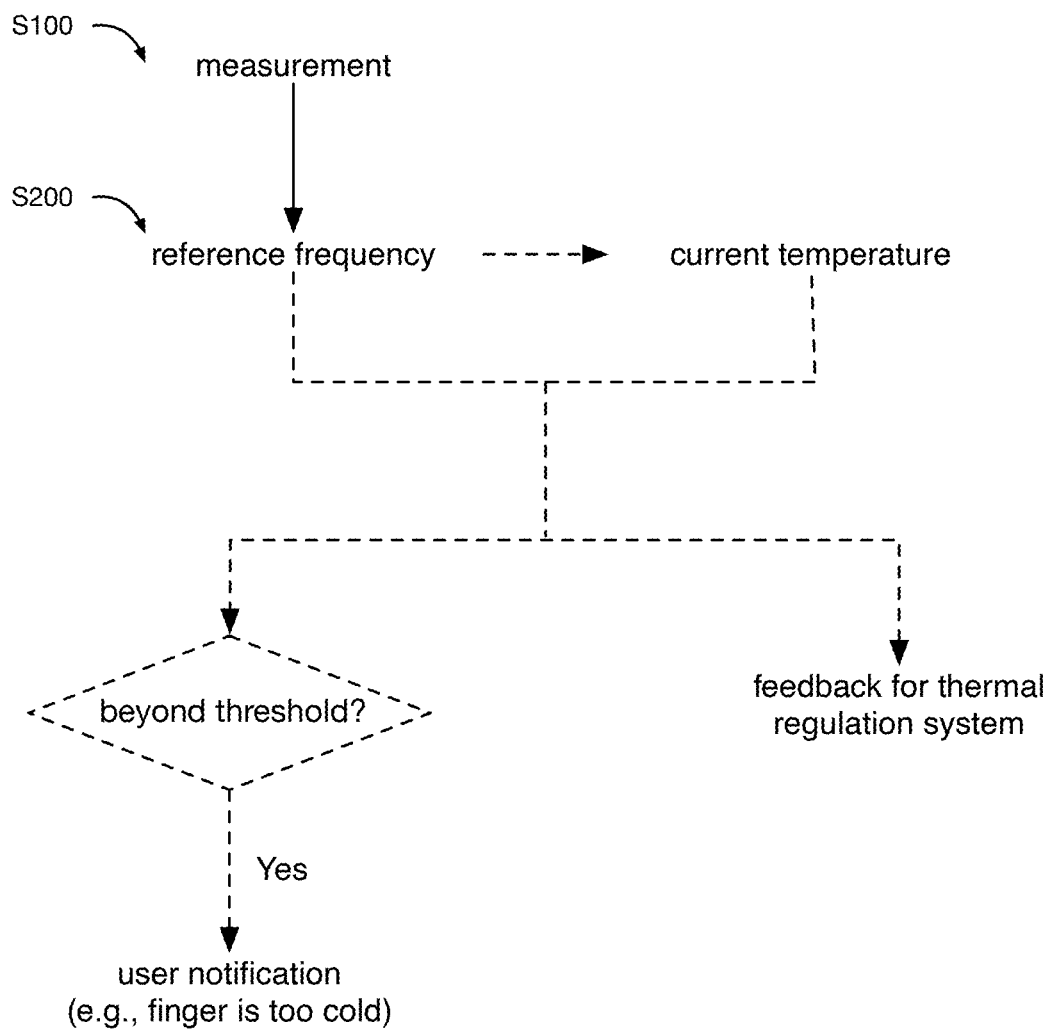
FIG. 8 depicts an example of using a reference frequency.

The system can optionally include a sensor, wherein sensor measurements can be used to: flag an error, notify a user (e.g., that the sample is too cold, that all or parts of the system are too cold, that a measurement is inaccurate, etc.), provide feedback to the thermal regulation system 600 (e.g., control the heater), tune the shimming system (e.g., adjust the shimming system parameters based on the reference frequency), process one or more measurements, and/or otherwise used. In a first variant, the sensor includes a temperature sensor, wherein the sensor measurements include temperature measurements. In a second variant, the sensor includes the receiver 400 (e.g., the sensor is the receiver 400), wherein the sensor measurements include NMR measurements. For example, a reference frequency can be determined based on one or more NMR measurements (e.g., a calibration measurement, an experiment measurement, etc.), wherein the reference frequency can be used as a proxy for temperature and/or temperature can be determined based on the reference frequency. In a first specific example, the thermal regulation system 600 can be controlled based on the reference frequency. In an illustrative example, the thermal regulation system 600 can use one or more proportional-integral-derivative controller (PID) controllers, wherein the reference frequency and/or a temperature determined based on the reference frequency can be used as feedback for the PID controller to maintain a target temperature (e.g., within an acceptable range of the target temperature such as ±5°, ±2°, ±1°, ±0.5°, etc.). In a second specific example, a user can be notified when the reference frequency (e.g., a calibration reference frequency and/or an experiment reference frequency) falls outside one or more criteria (e.g., above a threshold, below a threshold, etc.). The criteria can be predetermined (e.g., a predetermined threshold), relative (e.g., a change in frequency over time), and/or otherwise determined. An example is shown in FIG. 8. However, the sensor can be otherwise configured.

The processing system 500 (e.g., computing system) functions to determine the reference frequency, process measurements, adjust transmitter parameters and/or receiver parameters (e.g., electronics parameters), and/or perform any other functions. The processing system 500 can include one or more: CPUs, GPUs, custom FPGA/ASICS, microprocessors, servers, cloud computing, and/or any other suitable components. The processing system 500 can be local (e.g., embedded in the housing 200), remote, distributed, or otherwise arranged relative to any other system or module. However, the processing system 500 can be otherwise configured.

The system can include one or more models, including an analyte model, a reference frequency prediction model, and/or any other model. The models can include classical or traditional approaches, machine learning approaches, and/or be otherwise configured. The models can include regression (e.g., linear regression, non-linear regression, logistic regression, etc.), decision tree, LSA, clustering, association rules, dimensionality reduction (e.g., PCA, t-SNE, LDA, etc.), neural networks (e.g., CNN, DNN, CAN, LSTM, RNN, FNN, encoders, decoders, deep learning models, transformers, etc.), ensemble methods, optimization methods (e.g., Bayesian optimization), classification, rules, heuristics, equations (e.g., weighted equations, etc.), selection (e.g., from a library), lookups, regularization methods (e.g., ridge regression), Bayesian methods (e.g., Naiive Bayes, Markov), instance-based methods (e.g., nearest neighbor), kernel methods, support vectors (e.g., SVM, SVC, etc.), statistical methods (e.g., probability), comparison methods (e.g., matching, distance metrics, thresholds, etc.), deterministics, genetic programs, and/or any other suitable model.

Models can be trained, learned, fit, predetermined, and/or can be otherwise determined. The models can be trained or learned using: supervised learning, unsupervised learning, self-supervised learning, semi-supervised learning (e.g., positive-unlabeled learning), reinforcement learning, transfer learning, Bayesian optimization, fitting, interpolation and/or approximation (e.g., using gaussian processes), backpropagation, and/or otherwise generated.

Any model can optionally be trained, validated, verified, reinforced, calibrated, or otherwise updated based on newly received, up-to-date measurements; past measurements recorded during the operating session; historic measurements recorded during past operating sessions; or be updated based on any other suitable data. In a specific example, the analyte model can optionally be trained (e.g., calibrated) in a set of initial experiments with a known analyte level.

However, the system can be otherwise configured.

5. METHOD

As shown in FIG. 1, the method can include: sampling a calibration measurement S100, determining a reference frequency based on the calibration measurement S200, and sampling an experiment measurement S300. The method can optionally include processing the experiment measurement S400, determining an analyte level S500, and/or any other suitable steps.

All or portions of the method can be performed in real time (e.g., responsive to a request), iteratively, asynchronously, periodically, before and/or after every experiment, between every experiment, before and/or after every N experiments, between every N experiments, and/or at any other suitable time. All or portions of the method can be performed automatically, manually, semi-automatically, and/or otherwise performed.

All or portions of the method can be performed by one or more components of the system, using a computing system, using a database (e.g., a system database, a third-party database, etc.), by a user, and/or by any other suitable system.

Figure 4:
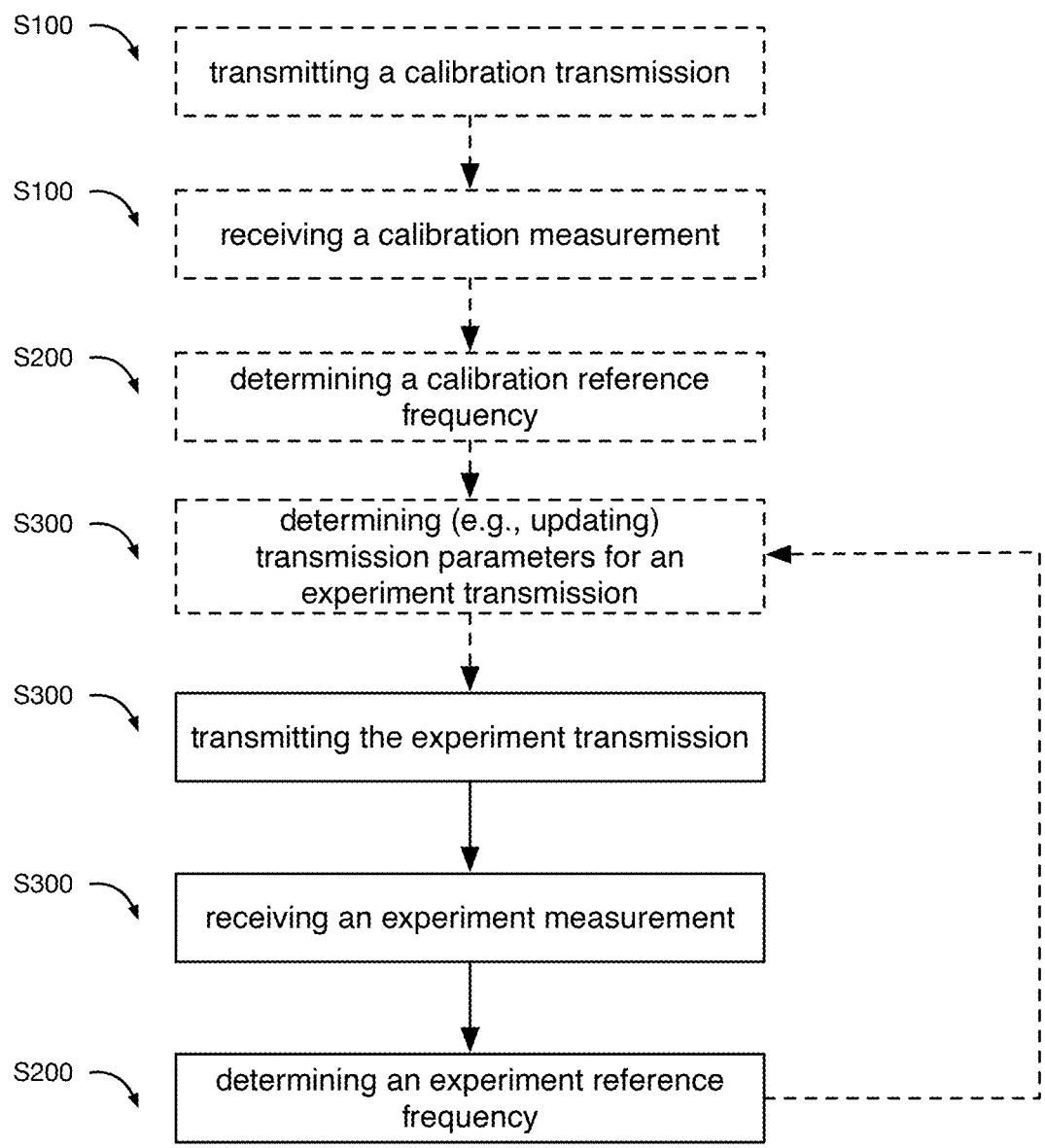
FIG. 4 is a schematic representation of an example of determining a reference frequency.

Sampling a calibration measurement S100 functions to acquire a signal in response to a calibration transmission. S100 can be performed before S200, before S300, during S300, after S300, and/or at any other time. The calibration measurement can optionally be an experiment measurement (e.g., wherein S100 includes S300, wherein S100 includes a first instance of S300, etc.). In an illustrative example, a measurement can function as both an experiment measurement (e.g., wherein a blood analyte level is determined from the measurement) and a calibration measurement (e.g., wherein a reference frequency determined from the measurement is used to determine a subsequent transmission and/or to process another measurement). An example is shown in FIG. 4.

Figure 9:
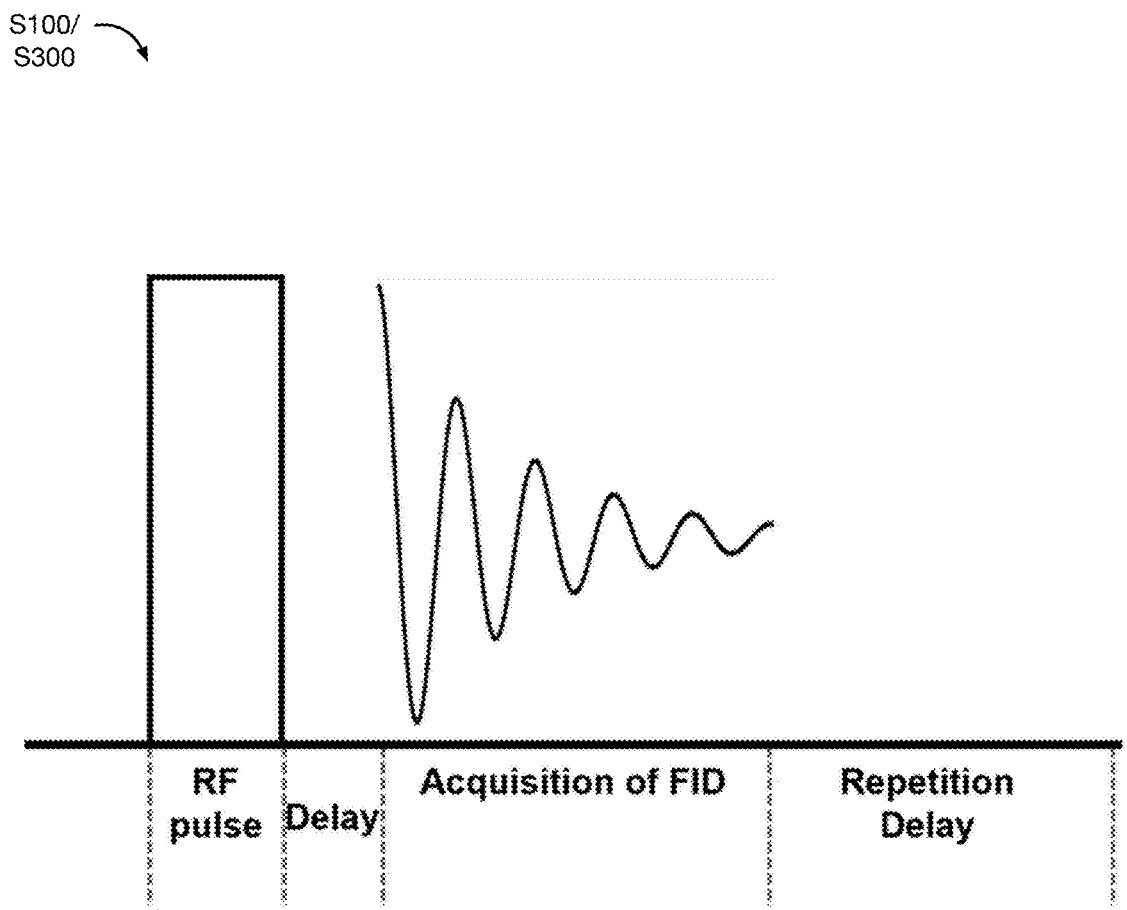
FIG. 9 depicts an example of sampling a calibration measurement.
Figure 16:
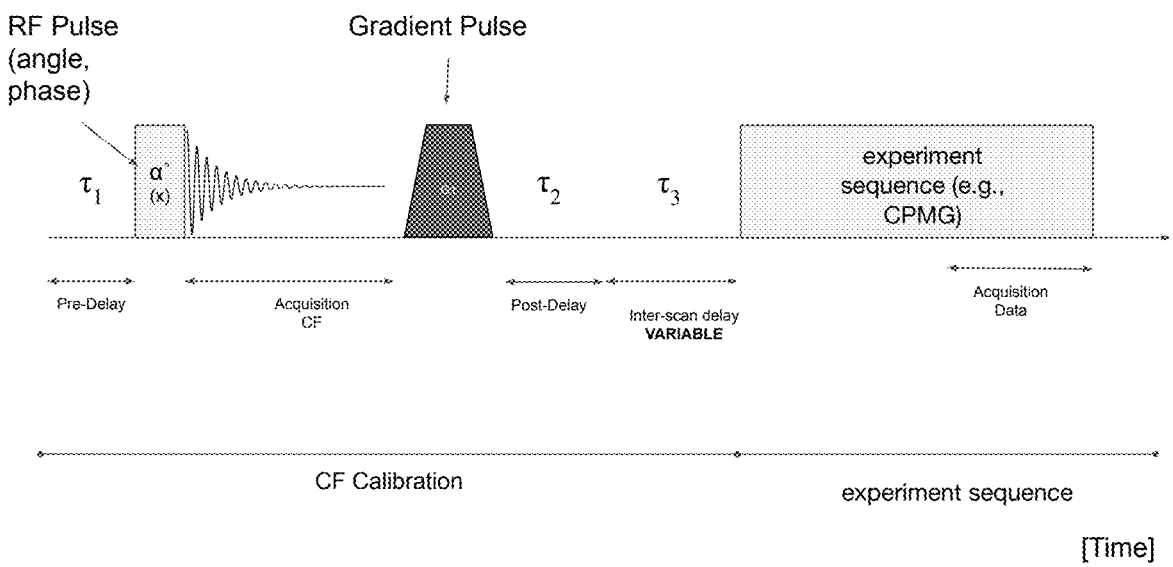
FIG. 16 depicts a specific example of a scan, including a calibration and an experiment.

Sampling a calibration measurement can include transmitting a calibration transmission (e.g., using the transmitter 300) to a sample, and receiving a calibration measurement from the sample in response to the calibration transmission (e.g., using the receiver 400); examples are shown in FIG. 9 and FIG. 16. S100 can optionally include a delay between transmitting the calibration transmission and receiving the calibration measurement. The delay can be between 0 ms-100 ms or any range or value therebetween (e.g., less than 50 ms, less than 25 ms, etc.), but can alternatively be greater than looms.

The transmission parameters for the calibration transmission can be determined based on: a previous iteration of all or parts of the method (e.g., a previously determined reference frequency); known, estimated, and/or predicted signal parameters for the calibration measurement (e.g., a predicted reference frequency); NMR system parameters, environment parameters (e.g., temperature); sample parameters; predetermined; random; and/or otherwise determined.

The characteristic frequency for the calibration transmission is preferably within a threshold range of the Larmor frequency of the NMR system and sample (e.g., the reference frequency determined via S200), but can alternatively be any other frequency. The threshold range can be between 0.05 ppm-50 ppm or any range or value therebetween (e.g., 0.1 ppm, 0.5 ppm, 1 ppm, 10 ppm, 25 ppm, etc.), but can alternatively be less than 0.05 ppm or greater than 50 ppm. The characteristic frequency for the calibration transmission can optionally be determined using methods in S300. In a first variant, the characteristic frequency can be a predetermined value. In a second variant, the characteristic frequency can be determined based on a previous sampled measurement (e.g., a previous iteration of S100, a previous iteration of S300, etc.; using methods described in S300). In a third variant, the characteristic frequency can be identified using a calibration frequency sweep. For example, a calibration frequency sweep can function to identify a characteristic frequency for the calibration transmission when the range of possible Larmor frequencies is large (e.g., after powering on the NMR system, for a first iteration of the method, etc.). The calibration frequency sweep can include iteratively performing S100 for a range of characteristic frequencies for calibration transmissions (e.g., wherein the range can be at least 10 kHz, at least at least 100 kHz, at least 1 MHz, at least 1.5 MHz, at least 2 MHz, etc.), wherein a characteristic frequency is selected from the range of characteristic frequencies based on the respective calibration measurements.

The characteristic frequency for the calibration transmission can be between 100 Hz-500 MHz or any range or value therebetween, but can alternatively be less than 100 Hz or greater than 500 MHz. The frequency bandwidth for the calibration transmission can be between 1 ppm-5000 ppm or any range or value therebetween (e.g., 10 ppm-1000 ppm, 100 ppm-500 ppm, 200 ppm, greater than 10 ppm, greater than 50 ppm, greater than 100 ppm, etc.), but can alternatively be less than 1 ppm or greater than 5000 ppm.

The transmission parameters for the calibration transmission preferably include a tip angle (e.g., flip angle) for the sample that is less than a threshold value (e.g., such that the tip angle is a small tip angle), but can alternatively result in any other tip angle (e.g., $\pi/2$). The tip angle threshold value can be between 0.1°-50° or any range or value therebetween (e.g., 0.5°, 1°, 2°, 5°, 10°, 20°, 45°, etc.), but can alternatively be less than 0.1° or greater than 50°. The tip angle can optionally be determined based on a previous measurement (e.g., based on a noise level in the previous measurement).

Sampling the calibration measurement can optionally include determining receiver parameters (e.g., acquisition time, receiver gain, etc.) to receive the calibration measurement. Receiver parameters can be determined based on: known, estimated, and/or predicted signal parameters for a measurement (e.g., a known, estimated, and/or predicted reference frequency); transmission parameters (e.g., characteristic frequency, tip angle, etc.); sample parameters; a signal decay rate, predetermined, random, a combination thereof, and/or otherwise determined.

A crusher transmission (e.g., crusher gradient) can optionally be transmitted before and/or after sampling the calibration measurement (e.g., before S300).

Calibration measurements can be processed (e.g., using S400 methods) or unprocessed measurements. A processed calibration measurement can optionally be used as an calibration measurement in all or parts of the method.

However, the calibration measurement can be otherwise sampled.

Determining a reference frequency based on the calibration measurement S200 functions to determine the Larmor frequency for the NMR system and sample. S200 can be performed after S100 and/or at any other time. S200 can be performed at the processing system (e.g., locally to the NMR system, remotely from the NMR system, a combination thereof, etc.).

The reference frequency can be a single value, a set of values, a range of values, and/or otherwise characterized. The reference frequency is preferably a frequency for a point of interest on the calibration measurement (e.g., the center frequency of the calibration measurement), but can alternatively be otherwise associated with the calibration measurement. The reference frequency is preferably determined with an error less than a threshold (e.g., 2 Hz, 1 Hz, 0.5 Hz, 0.25 Hz, etc.), but can be determined with any other error.

The reference frequency can optionally be determined based on a processed calibration measurement. Examples of a processing calibration measurement can include: sampling, smoothing, fitting to a function, taking a subset of the original measurement (e.g., a subset with signal amplitude greater than a threshold), transforming, processing using S400 methods, truncating, and/or otherwise processed. However, the reference frequency can additionally or alternatively be determined based on an unprocessed calibration measurement.

The reference frequency can optionally be determined based on a water component of the calibration measurement (e.g., a peak associated with water), a lipid component of the calibration measurement (e.g., a peak associated with lipids), an analyte component of the calibration measurement (e.g., a peak associated with an analyte), any other component of the calibration measurement, and/or the entire calibration measurement. In a first specific example, the reference frequency can be determined based on a water component of the calibration measurement for each iteration of the method. In a second specific example, the reference frequency can be determined based on a water component of the calibration measurement for a first iteration of the method, wherein a second reference frequency can be determined based on a lipid component of a subsequent experiment measurement (e.g., when the experiment transmission suppresses the water component). In a third specific example, the reference frequency can be determined based on a lipid component of the calibration measurement for each iteration of the method. In an illustrative example, the lipid component of the calibration measurement does not correspond to the maximum peak of the calibration measurement, and the lipid component of the experiment measurement does correspond to the maximum peak of the experiment measurement.

Figure 3:
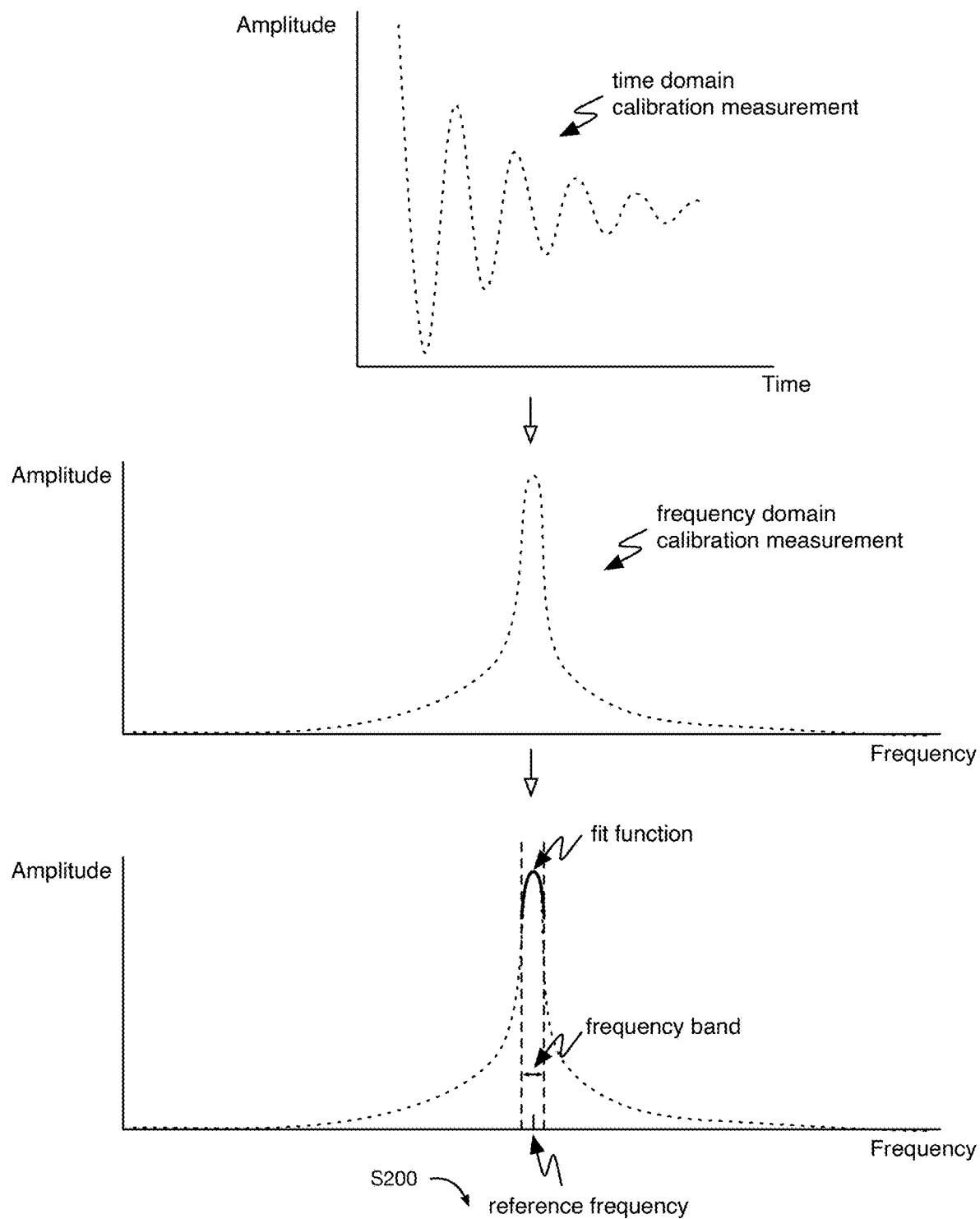
FIG. 3 depicts an illustrative example of determining a reference frequency.

In a first variant, the reference frequency is determined based on the calibration measurement transformed to the frequency domain. For example, a time domain (TD) calibration measurement can be transformed to a frequency domain (FD) calibration measurement using a Fourier transform (e.g., fast Fourier transform) and/or any other transform. In a first embodiment, the reference frequency can be the frequency corresponding to the maximum of the FD calibration measurement. In a second embodiment, a function (e.g., polynomial regression, linear regression, other regression, etc.) can be fit to all or a subset of the FD calibration measurement, wherein the reference frequency can be determined based on the fit function (e.g., example shown in FIG. 3). Examples of fit functions include Lorentzian, Gaussian, polynomials, nonlinear functions, combination functions, and/or any other functions. For example, the reference frequency can be the frequency corresponding to the maximum of the fit function. In examples, the subset of the FD calibration measurement can be a subset above a threshold amplitude, a specified number of points about the FD calibration measurement maximum (e.g., greater than 3 points, greater than 5 points, greater than 10 points, greater than 100 points, etc.), a subset within a frequency band, and/or any other subset.

In a specific example, the subset of the FD calibration measurement can be a segment of the calibration measurement, wherein the segment corresponds to a frequency band. The frequency band can be centered at the FD calibration measurement maximum, at a frequency corresponding to a component of the sample (e.g., water, lipids, an analyte, etc.), a predetermined frequency, and/or any other frequency of interest. For example, the frequency band can be centered at a peak corresponding to a component of the sample (e.g., a maximum of the raw data, a peak determined using interpolation of one or more points, etc.). The bandwidth for the frequency band can be predetermined, determined based on the calibration measurement (e.g., a percentage of the frequency range, full width at half maximum, etc.), and/or otherwise determined. The bandwidth can optionally be greater than a threshold, wherein the threshold can be between 0.005 ppm-10 ppm or any range or value therebetween (e.g., 0.01 ppm, 0.02 ppm, 0.05 ppm, 0.1 ppm, 0.2 ppm, 0.5 ppm, 1 ppm, 2 ppm, 5 ppm, 10 ppm, etc.). Additionally or alternatively, any other peak detection method can be used with the FD calibration measurement to determine the reference frequency.

In a second variant, the reference frequency is determined based on the TD calibration measurement. In examples, the reference frequency can be determined using zero crossing methods, peak-to-peak methods, shape analysis methods, rate of change, decay analysis methods (e.g., determining a decay for the TD calibration measurement), and/or any other frequency detection methods.

However, the reference frequency can be otherwise determined.

Figure 15:
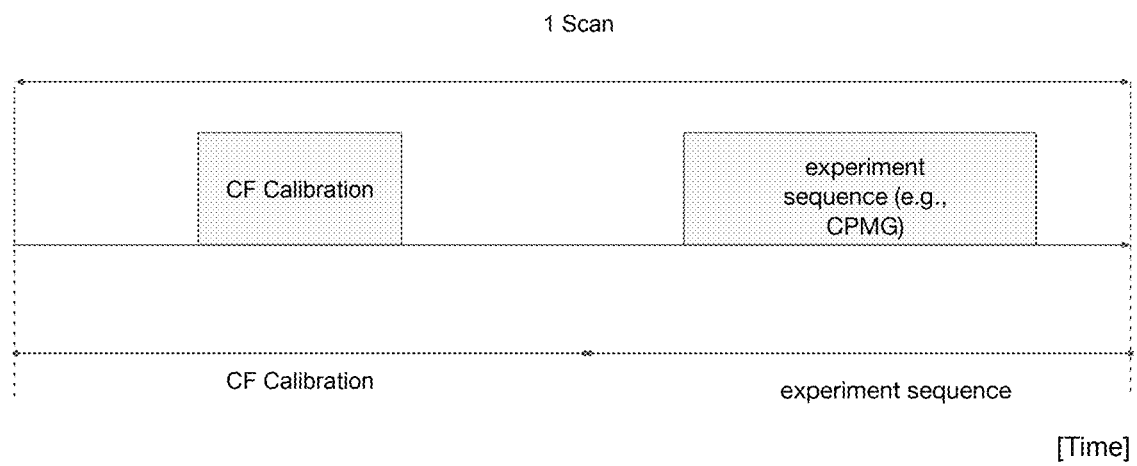
FIG. 15 depicts an example of a scan, including a calibration and an experiment.

Sampling an experiment measurement S300 functions to acquire a signal in response to an experiment transmission. S300 can be performed after S100, after S200, and/or at any other time. S300 can optionally be performed immediately after S100, after a delay after S100, and/or at any other time. Examples are shown in FIG. 15 and FIG. 16. The delay after S100 is preferably minimized, but can alternatively be any other delay time. Limiting factors in minimizing the delay can optionally include sample recovery time, acquisition time, processing time to determine the reference frequency, processing time to adjust the experiment transmission based on the frequency, and/or any other factors. The delay time is preferably less than a threshold, wherein the threshold can be between 10 ms-5 s or any range or value therebetween (e.g., 10 ms, 50 ms, 100 ms, 500 ms, 1 s, 1.5 s, 2 s, etc.), but the threshold can alternatively be less than 10 ms or greater than 5 s.

Figure 10A:
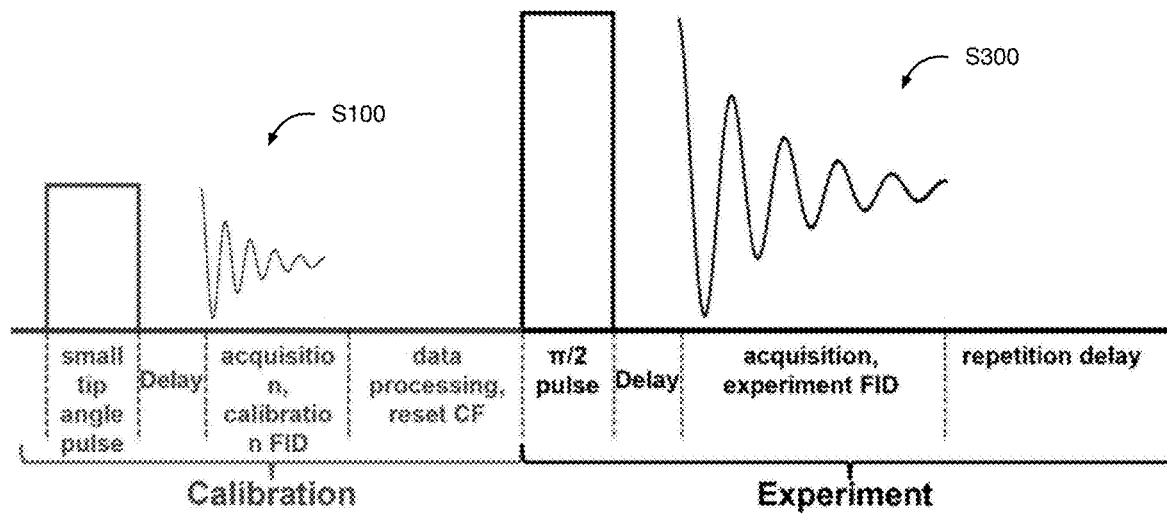
FIGS. 10A and 10B depict examples of sampling a calibration measurement before sampling an experiment measurement.
Figure 10B:
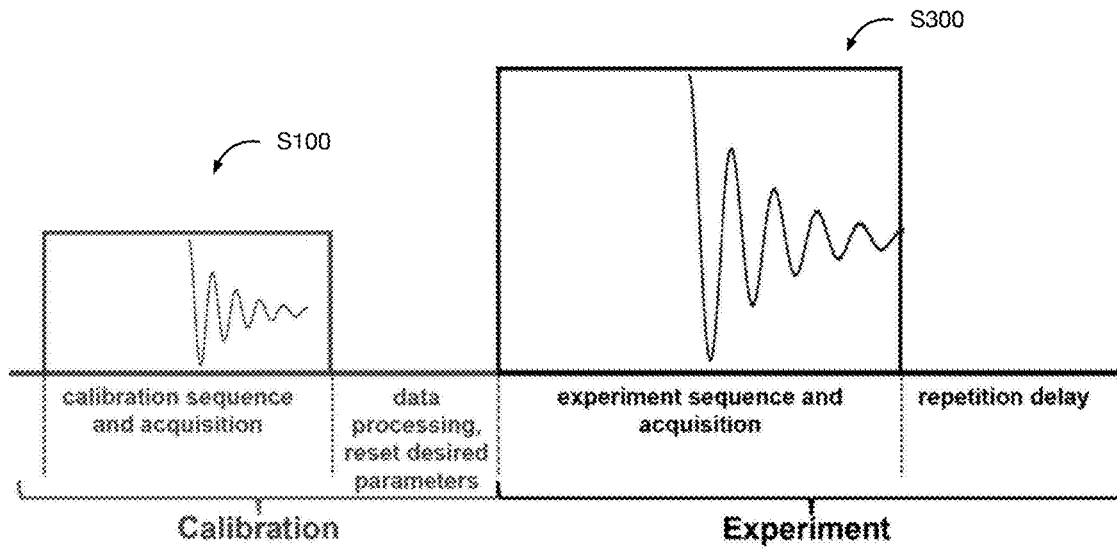

Sampling an experiment measurement can include transmitting an experiment transmission (e.g., using the transmitter 300) to a sample, and receiving an experiment measurement from the sample in response to the experiment transmission (e.g., using the receiver 400); examples are shown in FIG. 10A and FIG. 10B. S300 can optionally include a delay between receiving the experiment measurement and transmitting the experiment transmission.

The transmission parameters (e.g., the parameters defining the transmission portion of the experiment) can be determined based on: a previous iteration of all or parts of the method (e.g., a previously determined reference frequency); known, estimated, and/or predicted signal parameters for the experiment measurement (e.g., a predicted reference frequency); NMR system parameters (e.g., shimming), environment parameters (e.g., temperature); sample parameters; predetermined; random; and/or otherwise determined. For example, the experiment transmission can be determined (e.g., updated) based on one or more reference frequencies for prior measurements (e.g., at least 1, at least 2, at least 3, at least 4, at least 5, etc.). In a specific example, the transmission parameters (e.g., characteristic frequency, modulation frequency, etc.) for the experiment transmission can be determined based on the reference frequency determined in S200.

Figure 5A:
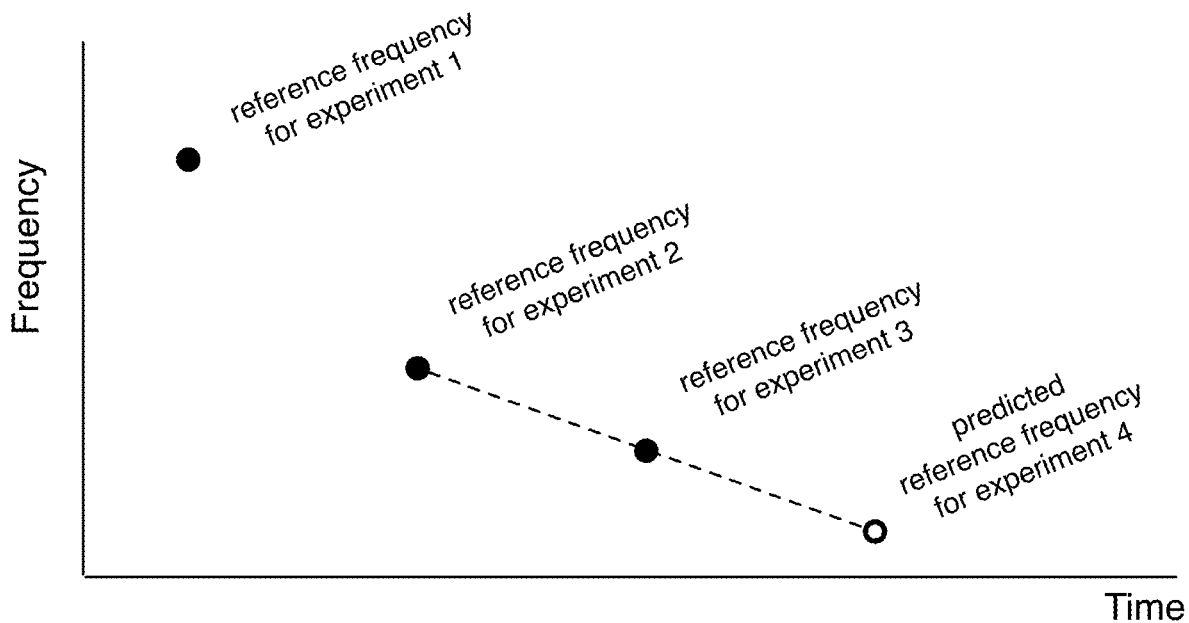
FIGS. 5A and 5B depict illustrative examples of determining an estimated reference frequency.
Figure 5B:
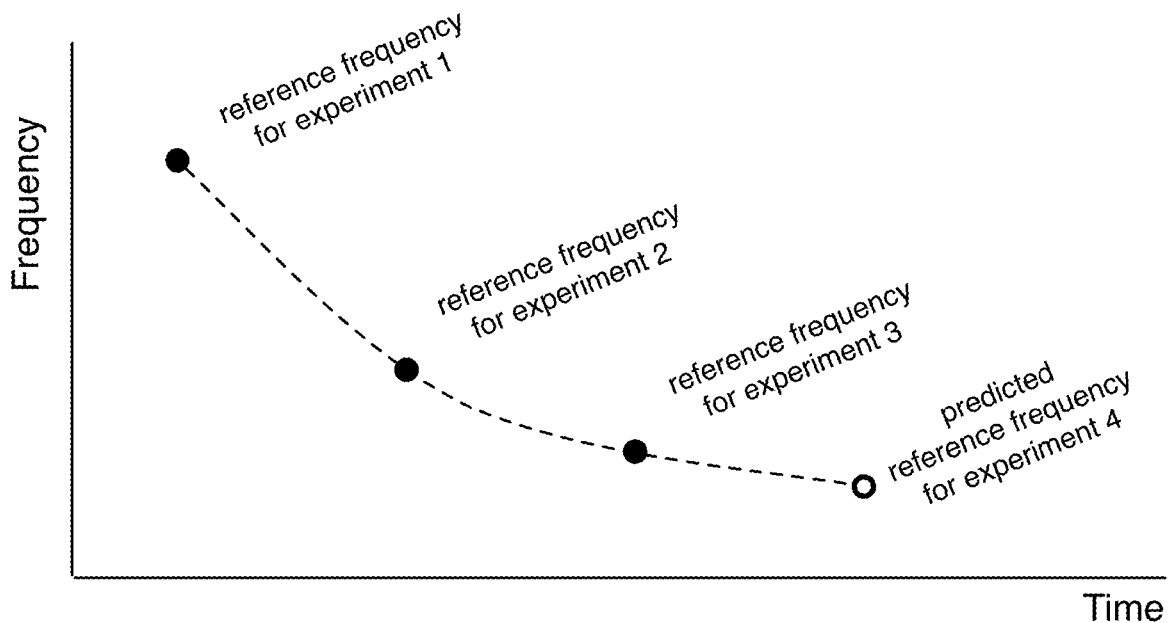

In a first variant, the characteristic frequency can be a predetermined value. In a second variant, the characteristic frequency can be determined based on a previous sampled measurement (e.g., S100, a previous iteration of S300, etc.). For example, S300 can include determining the experiment transmission characteristic frequency based on the reference frequency determined in S200. In a first embodiment, the characteristic frequency for the calibration transmission can be the reference frequency of the calibration measurement (e.g., wherein the Larmor frequency for the experiment measurement is predicted to be approximately the same as the Larmor frequency for the calibration measurement). In a second embodiment, the characteristic frequency can be a predicted reference frequency and/or estimated reference frequency based on the calibration reference frequency (e.g., the characteristic frequency is an adjusted calibration reference frequency). For example, the characteristic frequency can be the reference frequency for the calibration measurement adjusted based on an expected frequency drift and the delay between the experiment transmission and the calibration measurement. The expected frequency drift can optionally be determined based on one or more reference frequencies for prior measurements (e.g., at least 1, at least 2, at least 3, at least 4, etc.). In an example, the predicted reference frequency can be determined using a reference frequency prediction model. In a specific example, a function can be fit to the prior reference frequencies (e.g., from prior iterations of all or parts of the method), wherein the characteristic frequency can be a predicted reference frequency for the current time, determined using the fit function. The fit function can be linear (e.g., example shown in FIG. 5A) or nonlinear (e.g., example shown in FIG. 5B).

A modulation frequency (e.g., a modulating transmit frequency) can optionally be applied to the experiment transmission (e.g., to modulate the characteristic frequency over time). In an example, the modulation frequency can be an expected frequency drift or be determined based on an expected frequency drift.

The characteristic frequency for the experiment transmission can be between 100 Hz-500 MHz or any range or value therebetween (e.g., 500 Hz-5000 Hz, 1000 Hz, etc.), but can alternatively be less than 100 Hz or greater than 500 MHz.

The frequency bandwidth for the experiment transmission (e.g., about the characteristic frequency) can be between 0.01 ppm-1000 ppm or any range or value therebetween (e.g., 0.01 ppm-10 ppm, 1 ppm-100 ppm, less than 10 ppm, less than 50 ppm, less than 100 ppm, etc.), but can alternatively be less than 0.01 ppm or greater than 1000 ppm.

The transmission parameters for the experiment transmission preferably include a tip angle for the sample that is greater than a threshold value (e.g., such that the tip angle is a large tip angle), but can alternatively result in any other tip angle. The tip angle threshold value can be between 0.1°-50° or any range or value therebetween (e.g., 1°, 2°, 5°, 10°, 20°, 45°, etc.), but can alternatively be less than 0.1° or greater than 50°.

Sampling the experiment measurement can optionally include determining receiver parameters (e.g., acquisition time, receiver gain, etc.) to receive the experiment measurement. Receiver parameters can be determined based on: known, estimated, and/or predicted signal parameters for a measurement (e.g., a known, estimated, and/or predicted reference frequency); transmission parameters (e.g., characteristic frequency, tip angle, etc.); sample parameters; a signal decay rate, predetermined, random, a combination thereof, and/or otherwise determined. For example, receiver parameters can be adjusted for the experiment measurement based on the reference frequency determined in S200.

Experiment measurements can be processed (e.g., using S400 methods) or unprocessed measurements. A processed experiment measurement can optionally be used as an experiment measurement in all or parts of the method.

However, the experiment measurement can be otherwise sampled.

Figure 12A:
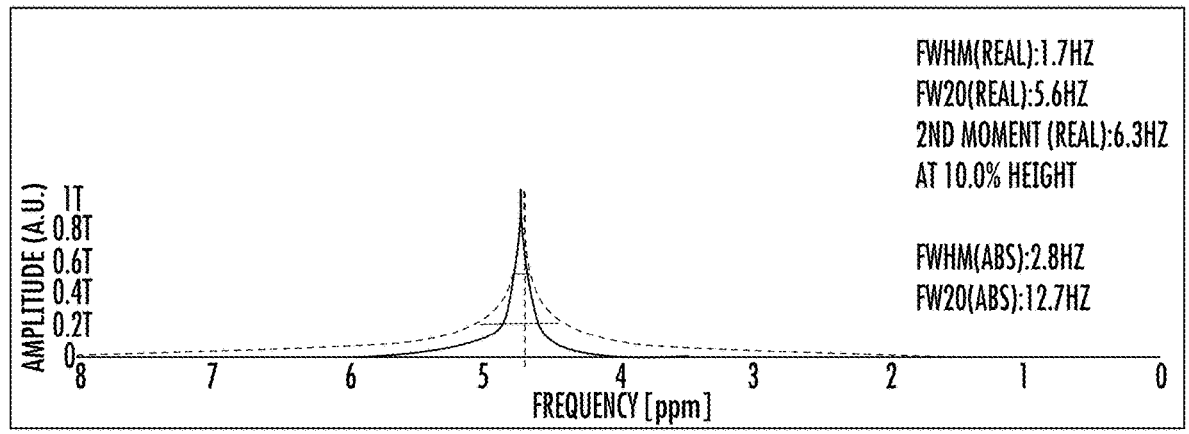
FIG. 12A depicts an illustrative example of an experiment measurement unaffected by frequency drift.
Figure 12B:
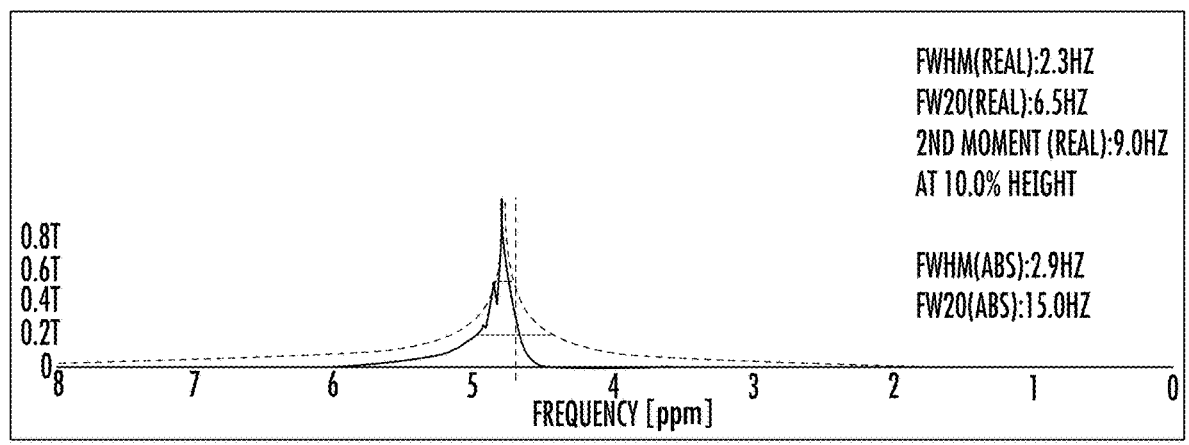
FIG. 12B depicts an illustrative example of an experiment measurement affected by frequency drift.

The method can optionally include processing the experiment measurement S400, which functions to correct the experiment measurement for drift during the experiment (e.g., chirp correction). S400 can be performed after S300, after S200 (e.g., after a second iteration of S100 and S200), after all iterations are complete, and/or at any other time. In a specific example, for a set of experiment measurements, each experiment measurement can be processed, a subset of experiment measurements (e.g., one or more selected experiment measurements) can be processed, and/or any other experiment measurement can be processed. An example of an experiment measurement without frequency drift is shown in FIG. 12A. An example of an experiment measurement with frequency drift is shown in FIG. 12B.

S400 can optionally include: determining a frequency drift, and processing the experiment measurement based on the frequency drift. The frequency drift can be an absolute drift over the experiment, a frequency drift rate, a function defining the frequency drift over time (e.g., over the course of the experiment), and/or be otherwise defined.

In a first variant, the frequency drift can be determined based on an analysis of a calibration measurement and/or an experiment measurement. For example, the analysis can include Fourier analysis (e.g., Fourier transform, short-time Fourier transform), regression, and/or any other signal processing or analysis methods. In a specific example, a short-time Fourier transform can be used to determine a rate of change of the frequency (e.g., frequency drift rate). The rate of change of the frequency can be linear, nonlinear, and/or defined by any other frequency drift function.

In a second variant, the frequency drift can be determined based on a first reference frequency (e.g., pre-experiment reference frequency) and a second reference frequency (e.g., post-experiment reference frequency). The first reference frequency can be determined (via S200 methods) based on a first calibration measurement sampled prior to the experiment transmission. However, the first reference frequency can additionally or alternatively be determined based on the experiment measurement (e.g., an initial section of the experiment measurement), based on a previous experiment measurement, and/or otherwise determined. The second reference frequency is preferably determined (via S200 methods) based on a second calibration measurement sampled after the experiment transmission, but can alternatively be otherwise determined. For example, a second iteration of S100 and S200 can be performed after S300 to determine the second reference frequency. The second iteration of S100 can optionally use a characteristic frequency for the second calibration transmission based on (e.g., equal to) the characteristic frequency for the first calibration transmission and/or the first reference frequency. However, the second reference frequency can additionally or alternatively be determined based on the experiment measurement (e.g., an end section of the experiment measurement), based on a subsequent experiment measurement, and/or otherwise determined.

Figure 14A:
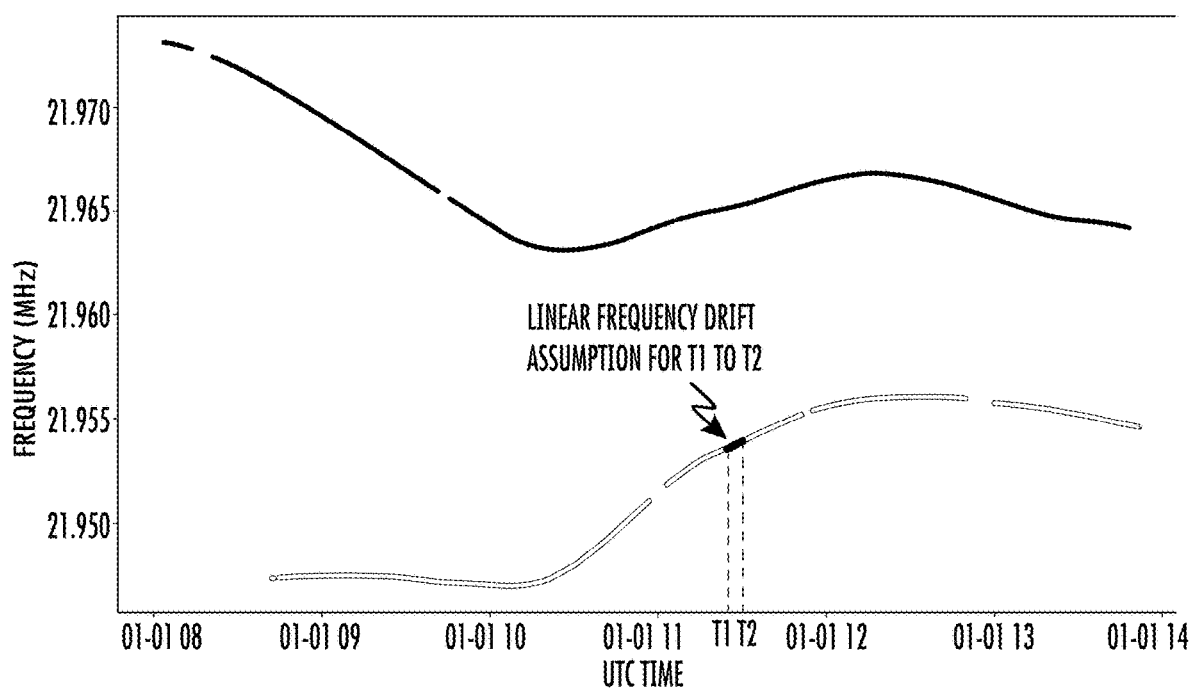
FIG. 14A depicts an illustrative example of linear frequency drift over time.
Figure 14B:
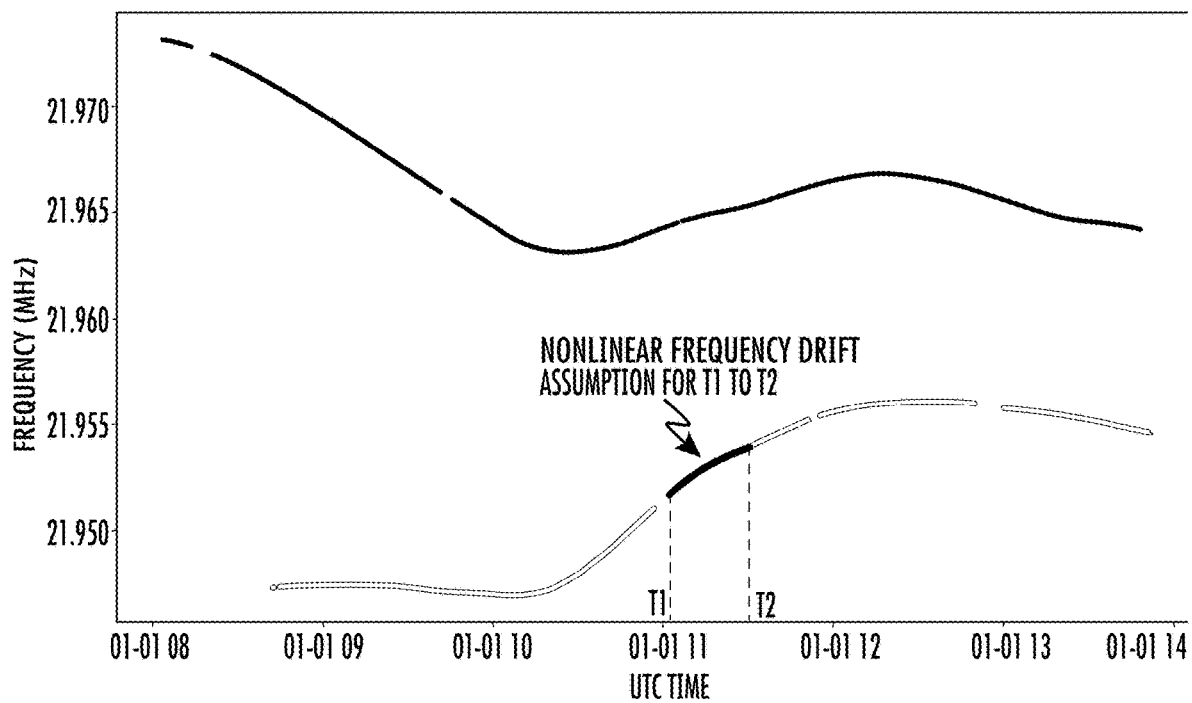
FIG. 14B depicts an illustrative example of nonlinear frequency drift over time.

Determining a frequency drift can include determining a function defining the frequency drift (e.g., based on the first reference frequency and the second reference frequency, based on an analysis of a measurement, etc.). In a first variant, the frequency drift is assumed to be linear (e.g., example shown in FIG. 14A). The linear assumption can optionally be applied for experimental time scales of less than a threshold value (e.g., 30 seconds, 1 minute, 100 seconds, 5 minutes, 10 minutes, 1 hour, etc.). In a specific example, the frequency drift rate can be: $r=(f_2-f_1)/(t_2-t_1)$ where $f_1$ is the first reference frequency determined using a measurement (e.g., the first calibration measurement) sampled at time $t_1$, and $f_2$ is the second reference frequency, determined using a measurement (e.g., the second calibration measurement) sampled at time $t_2$. In a second variant, the frequency drift is assumed to be nonlinear (e.g., example shown in FIG. 14B). For example, additional reference frequencies can be used to determine a nonlinear frequency drift. The additional reference frequencies can be determined based on: the experiment measurement, prior and/or subsequent experiment measurements, prior and/or subsequent calibration measurements, and/or otherwise determined. In a specific example, a nonlinear function can be fit to the multiple reference frequencies (e.g., three or more reference frequencies).

Figure 7:
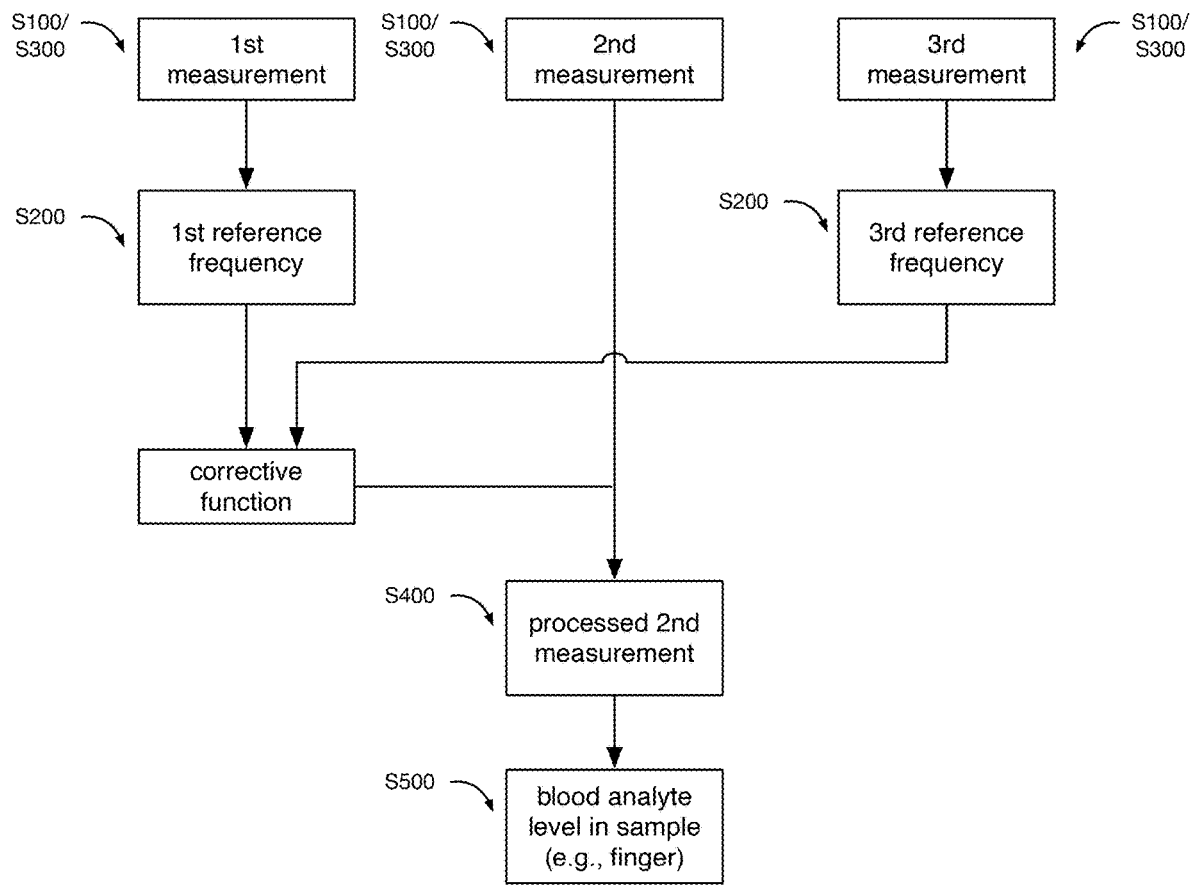
FIG. 7 depicts an example of determining a blood analyte level.
Figure 13:
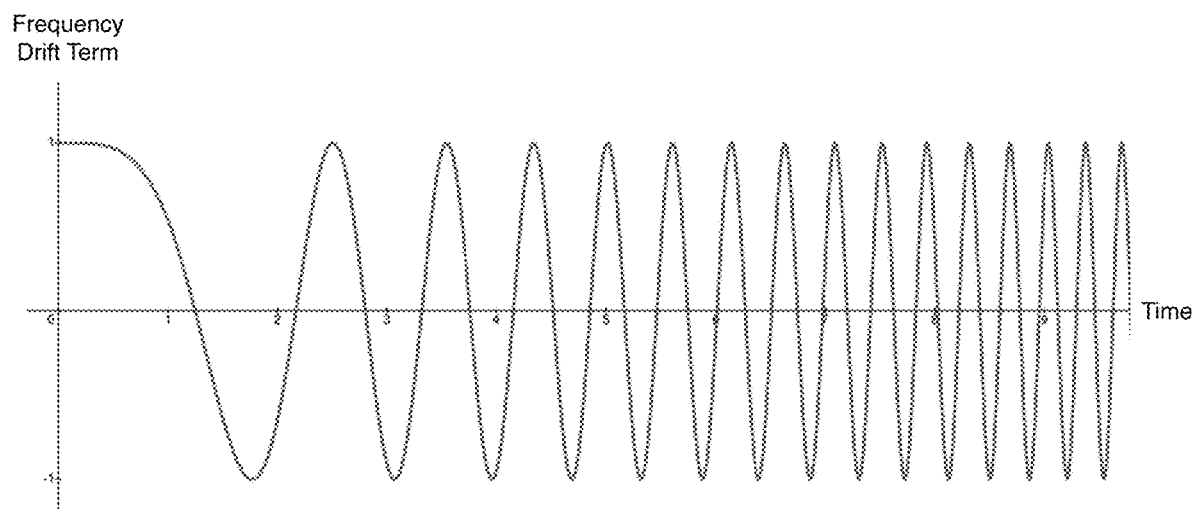
FIG. 13 depicts an illustrative example of a frequency drift term plotted with respect to time.

Processing the experiment measurement based on the frequency drift can include: determining a corrective function (e.g., corrective filter) based on the frequency drift (e.g., to filter out a frequency drift term from the experiment measurement), and applying the corrective function to experiment measurement. An example is shown in FIG. 7. In an illustrative example, the experiment measurement includes an underlying signal convolved with a frequency drift term (e.g., a chirp term), wherein the corrective function is used to deconvolve the experiment measurement, producing the underlying signal without frequency drift (e.g., a chirp corrected signal). An example of a frequency drift term plotted with respect to time is shown in FIG. 13. For example, for a linear frequency drift (e.g., a linear frequency drift and assuming the experiment measurement is composed of a sum of decaying exponentials), the corrective function can be: $F_{corr}(t)=e^{-irt}$ where t is the time after sampling a measurement (e.g., the first calibration measurement) used to determine the first reference frequency and r is the drift rate (e.g., in Hz/s). In an example, the corrective function can take on the form $F_{corr}(t)=e^{-i\varphi(t)}$ where $\varphi(t)$ is the signal phase over time and can be calculated by $\varphi(t) = \int_{t_0}^{t_1} f(t)dt$ where $f(t)$ is the frequency as a function of time, at times between $t_0$ and $t_1$. The corrective function is preferably applied to the experiment measurement in the time domain, but can alternatively be applied in the frequency domain and/or otherwise applied. In a specific example, applying the corrective function can include multiplying the experiment measurement and the corrective function.

S400 can additionally or alternatively include normalizing, transforming, aggregating, filtering, feature extraction, statistical analysis, downsampling, and/or any other signal processing and/or signal analysis methods. In an example, measurements can be downsampled to a sampling rate between 0.1 µs-0.1 s or any range or value therebetween (e.g., 10 µs-200 µs, etc.), but can alternatively be less than 0.01 µs or greater than 0.1 s.

However, the experiment measurement can be otherwise processed.

The method can optionally include determining an analyte level S500, which functions to quantify analyte content in the sample. S500 can be performed after S300 (e.g., after one or more iterations of S300), after S400, and/or at any other time. In examples, the analyte level can be a concentration, a percentage, a proportion, an abundance, an amount (e.g., mass, moles, etc.), and/or any other quantification of analyte content within the sample. Analyte levels can be absolute and/or relative (e.g., relative to a calibration analyte level). Examples of analytes in the sample include: glucose, methylsulfonylmethane (MSM), cholesterol, any blood metabolite, a proxy for an analyte (e.g., glucose proxy), and/or any other component.

The analyte level can be determined based on one or more measurements (e.g., processed and/or unprocessed experiment measurements). For example, the analyte level can be determined based on signal parameters of the one or more experiment measurements. Examples of signal parameters include: maximum signal intensity, signal shape (e.g., area under the curve, full width at half maximum, etc.), relative parameters (e.g., height) between components (e.g., between an analyte component and a lipid component, between an analyte component and a water component, between a lipid component and a water component, etc.), percentage of the signal from blood, echo time, relaxation time (e.g., T2 relaxation, T2* relaxation, T1 relaxation, etc.), and/or any other signal parameters.

In a first variant, the analyte level can be determined based on a single experiment measurement (e.g., one received signal, wherein the signal can optionally be processed using S400). For example, the analyte level can be determined by: determining signal parameters for all or a portion of the experiment measurement (e.g., for a component of the experiment measurement corresponding to the analyte), and determining the analyte level based on the signal parameters, using the analyte model.

In a second variant, the analyte level can be determined based on multiple experiment measurements (e.g., multiple received signals corresponding to different times, wherein each signal can optionally be processed using S400). In a first embodiment, the analyte level can be an aggregate analyte level across the multiple experiment measurements. In a first example, an analyte level can be determined for each experiment measurement, wherein the analyte levels are aggregated (e.g., averaging, weighted averaging, etc.) to determine an overall analyte level. In a second embodiment, the analyte level can be tracked across the multiple experiment measurements (e.g., to determine an analyte level trend over time). In a third example, multiple experiment measurements can be aggregated (e.g., averaging, weighted averaging, etc.), wherein the analyte level can be determined based on the aggregated measurements.

In a third variant, one or more experiment measurements of interest can be selected from a set of experiment measurements, wherein the analyte level can be determined based on the experiment measurement(s) of interest (e.g., using methods in the first variant and/or the second variant). The experiment measurement(s) of interest can be selected using a set of heuristics, criteria, a model, and/or any other selection methods. For example, the experiment measurement(s) can be selected based on one or more signal parameters of the measurement and/or a portion thereof (e.g., a water component, a lipid component, etc.).

However, an analyte level can be otherwise determined.

Figure 11A:
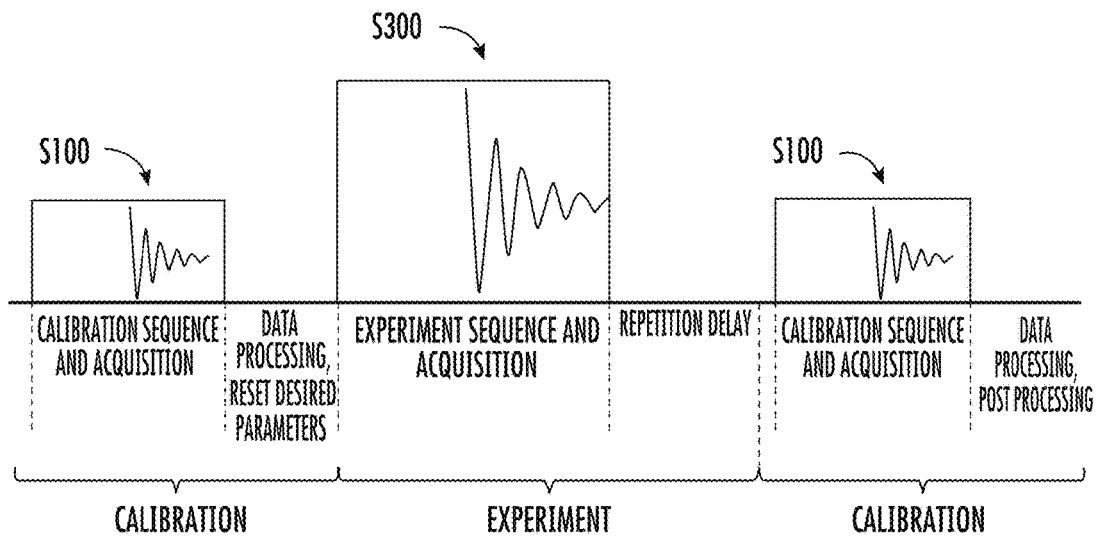
FIG. 11A depicts an example of sampling a calibration measurement before and after sampling an experiment measurement.
Figure 11B:
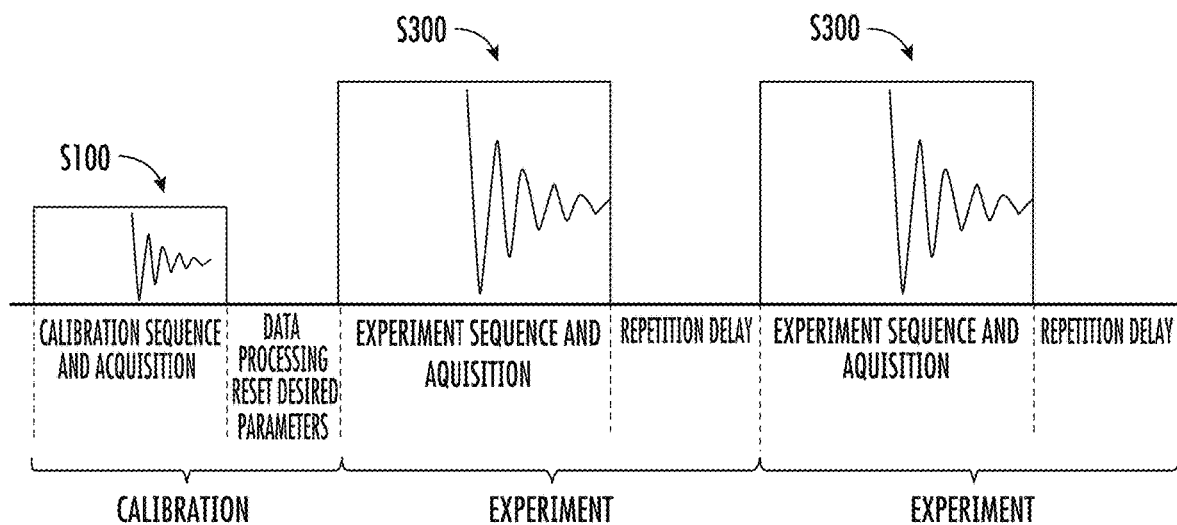
FIG. 11B depicts an example of sampling a calibration measurement before and sampling a set of experiment measurements.
Figure 11C:
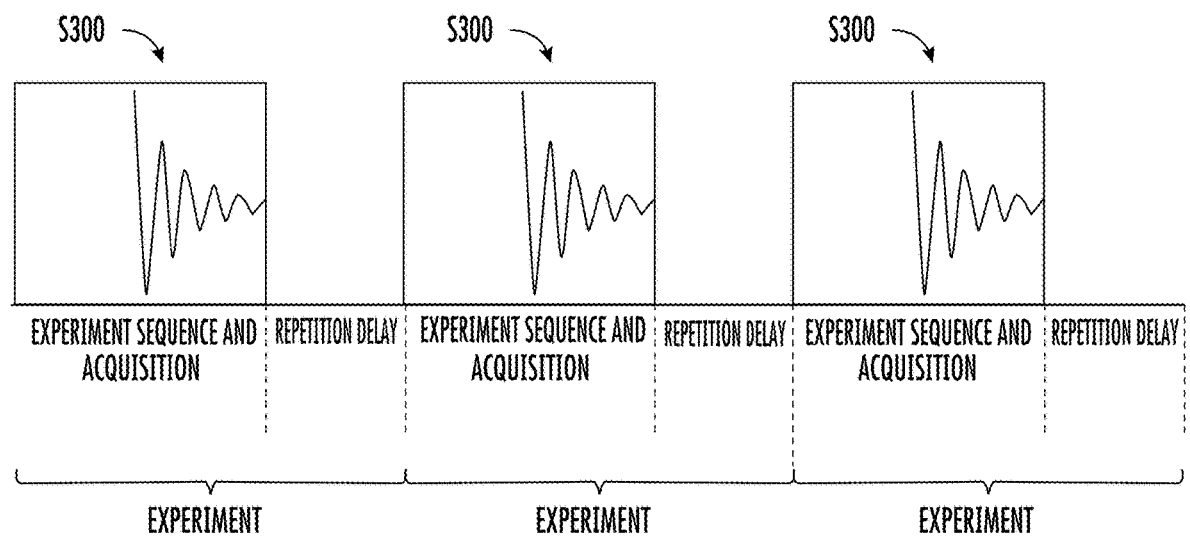
FIG. 11C depicts an example of sampling a set of experiment measurements.

All or parts of the method can optionally be performed iteratively. For example, all or portions of the method can be iteratively performed for a set of experiments and a corresponding set of experiment measurements, wherein the number of experiments (and corresponding experiment measurements) can be between 1 and 1000 or any range or value therebetween (e.g., at least 2, at least 3, at least 4, at least 5, at least 10, etc.), but can alternatively be greater than 1000. The delay between each experiment can be between 5 ms-100 hours or any range or value therebetween (e.g., 10 ms-1000 ms, 10 ms-10 s, 20 ms-5 s, at least 100ms, at least is, at least 10 s, at least 1 hour, at least 4 hours, at least 12 hours, etc.), but can alternatively be less than 5 ms or greater than 100 hrs. Examples are shown in FIG. 11A, FIG. 11B, and FIG. 11C.

Figure 6:
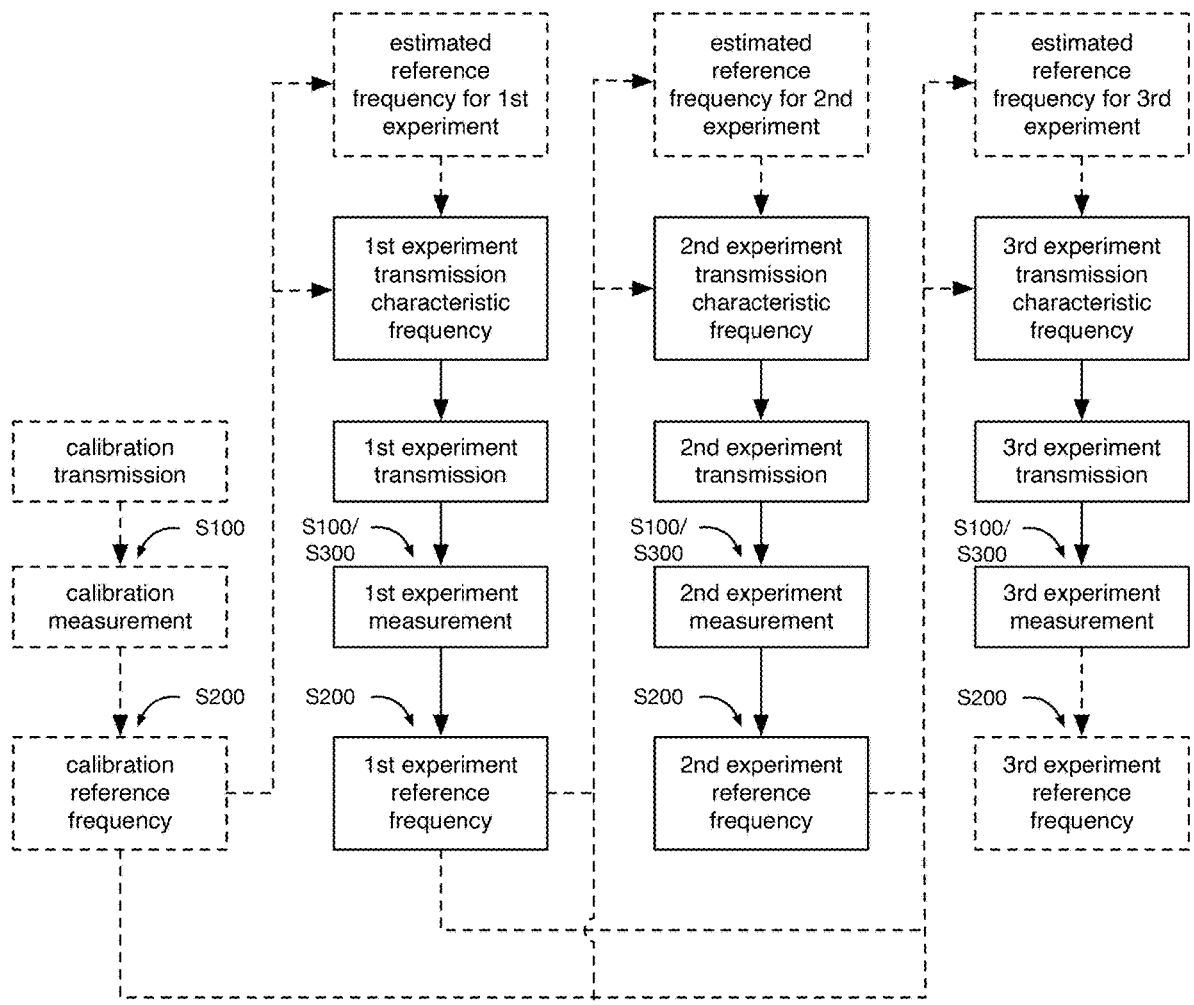
FIG. 6 depicts an example of iteratively determining a set of experiment measurements.

For example, the method can include determining a set of experiment measurements, which can include iteratively: transmitting an experiment transmission; sampling an experiment measurement (e.g., experiment signal) from the sample in response to the experiment transmission; determining a reference frequency based on the experiment measurement; and determining an updated experiment transmission based on the reference frequency (e.g., adjusting the characteristic frequency for the experiment transmission based on the reference frequency), wherein the updated experiment transmission is used as the experiment transmission in a subsequent iteration. In a specific example, each experiment measurement can optionally function as a calibration measurement for a subsequent measurement and/or previous measurement. An example is shown in FIG. 6.

In a specific example, a first iteration of the method includes transmitting a calibration transmission; sampling a calibration measurement (e.g., calibration signal); and determining a calibration reference frequency based on the calibration measurement. A second iteration of the method can include transmitting an experiment transmission, wherein the experiment transmission is determined based on the reference frequency for the calibration measurement; and sampling an experiment measurement. The method can optionally include one or more subsequent iterations, each including: transmitting an experiment transmission, wherein the experiment transmission is determined based on the reference frequency for one or more previous measurements; and sampling an experiment measurement. In an illustrative example, the experiment transmission (for an iteration of interest) can be determined using a reference frequency predicted based on the reference frequency for one or more prior iterations (e.g., at least one prior iterations, at least 2 prior iterations, at least 3 prior iterations, etc.). The method can optionally include a final iteration, including: transmitting a second calibration transmission; sampling a second calibration measurement; and determining a second calibration reference frequency based on the second calibration measurement. One or more experiment measurements can optionally be processed (e.g., using S400 methods) using one or more reference frequencies for prior measurements (e.g., at least 1, at least 2, at least 3, at least 4, etc.) and/or one or more reference frequencies for subsequent measurements (e.g., at least 1, at least 2, at least 3, at least 4, etc.). For example, the experiment measurement(s) can be processed after all experiments are sampled, immediately after each respective experiment measurement is sampled, and/or at any other time.

Different subsystems and/or modules discussed above can be operated and controlled by the same or different entities. In the latter variants, different subsystems can communicate via: APIs (e.g., using API requests and responses, API keys, etc.), requests, and/or other communication channels.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
   determining a set of experiment signals, wherein the set of experiment signals comprises at least three experiment signals, wherein determining each experiment signal in the set of experiment signals comprises:
      transmitting an experiment transmission using a nuclear magnetic resonance (NMR) system; and
      using the NMR system, sampling the experiment signal from a sample in response to the experiment transmission;
      determining a reference frequency for each experiment signal in the set of experiment signals;
   determining an updated experiment transmission, comprising:
      using a nonlinear prediction model, predicting an updated reference frequency based on the reference frequency for each experiment signal in the set of experiment signals;
      determining a characteristic frequency for the updated experiment transmission based on the updated reference frequency; and
      determining the updated experiment transmission based on the characteristic frequency;
   determining a subsequent experiment signal, wherein determining the subsequent experiment signal comprises:
      transmitting the updated experiment transmission using the NMR system; and
      using the NMR system, sampling the subsequent experiment signal from the sample in response to the updated experiment transmission; and
   determining a blood analyte level based on each experiment signal in the set of experiment signals and the subsequent experiment signal.

2. The method of claim 1, further comprising:
   transmitting a calibration transmission using the NMR system;
   using the NMR system, sampling a calibration signal from the sample in response to the calibration transmission; and
   determining a calibration reference frequency based on the calibration signal, wherein the calibration reference frequency is used to determine an experiment transmission for an experiment signal of the set of experiment signals.

3. The method of claim 2, wherein the calibration transmission comprises a frequency bandwidth greater than 10 ppm, and wherein each experiment transmission comprises a frequency bandwidth less than 10 ppm.

4. The method of claim 1, further comprising:
   determining a corrective function based on the reference frequency for each experiment signal in the set of experiment signals; and
   applying the corrective function to the subsequent experiment signal to determine a processed experiment signal, wherein determining the blood analyte level in the sample comprises determining the blood analyte level based on the processed experiment signal.

5. The method of claim 1, wherein the sample comprises an appendage of a user.

6. The method of claim 1, wherein the blood analyte comprises glucose.

7. A nuclear magnetic resonance (NMR) system, comprising:
   a transmitter;
   a receiver; and
   a processing system, configured to:
      determine a set of experiment signals, wherein the set of experiment signals comprises at least three experiment signals, wherein determining each experiment signal in the set of experiment signals comprises:
         using the transmitter, transmitting an experiment transmission for a current iteration; and
         using the receiver, sampling the experiment signal from a sample in response to the experiment transmission;

for each experiment signal in the set of experiment signals, determine a reference frequency based on the experiment signal;

using a nonlinear prediction model, predict an updated reference frequency based on the reference frequencies;

determine a characteristic frequency based on the updated reference frequency;

determine an updated experiment transmission based on the characteristic frequency;

transmit the updated experiment transmission using the NMR system;

using the NMR system, sample a subsequent experiment signal from the sample in response to the updated experiment transmission; and determine a blood analyte level based on each experiment signal in the set of experiment signals and the subsequent experiment signal.

8. The NMR system of claim 7, further comprising:

using the transmitter, transmitting a calibration transmission;

using the receiver, sampling a calibration signal from the sample in response to the calibration transmission; and determining a calibration reference frequency based on the calibration signal, wherein the calibration reference frequency is used to determine an experiment transmission for an experiment signal of the set of experiment signals.

9. The NMR system of claim 8, wherein the calibration transmission induces a tip angle of less than 45°, and wherein each experiment transmission induces a tip angle of greater than 45°.

10. The NMR system of claim 7, wherein, for each experiment signal in the set of experiment signals, determining the reference frequency based on the experiment signal comprises fitting a function to a segment of the experiment signal, wherein the segment corresponds to a frequency band, wherein the reference frequency corresponds to a maximum of the fit function.

11. The NMR system of claim 10, wherein the frequency band has a bandwidth greater than 0.01 ppm.

12. The NMR system of claim 7, further comprising a heater, wherein the heater is controlled based on the reference frequencies.

13. The NMR system of claim 7, further comprising a set of permanent magnets configured to generate a magnetic field over a target region of the sample.

* * * * *

UNITED STATES PATENT AND TRADEMARK OFFICE
CERTIFICATE OF CORRECTION

PATENT NO. : 12,306,276 B2
APPLICATION NO. : 18/503909
DATED : May 20, 2025
INVENTOR(S) : Nashman et al.

Page 1 of 1

It is certified that error appears in the above-identified patent and that said Letters Patent is hereby corrected as shown below:

In the Claims

Column 18, Line 64, In Claim 7, delete "transmission for a current iteration;" and insert --transmission;-- therefor Signed and Sealed this
First Day of July, 2025

Coke Morgan Stewart
*Acting Director of the United States Patent and Trademark Office*